United States Patent
Araki et al.

(10) Patent No.: US 7,398,193 B2
(45) Date of Patent: *Jul. 8, 2008

(54) METHOD OF OFFERING WALL-THICKNESS THINNING PREDICTION INFORMATION, AND COMPUTER-READABLE RECORDING MEDIUM STORING WALL-THICKNESS THINNING PREDICTION PROGRAM, AND METHOD OF PLANNING PIPING WORK PLAN

(75) Inventors: Kenji Araki, Mito (JP); Masatoshi Takada, Hitachi (JP); Masakazu Hisatsune, Hitachi (JP); Satoru Aoike, Hitachi (JP); Kenji Utaka, Hitachi (JP); Masafumi Noujima, Hitachi (JP); Chikara Takeuchi, Hitachi (JP)

(73) Assignee: Hitachi-GE Nuclear Energy, Ltd., Ibaraki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/451,376

(22) Filed: Jun. 13, 2006

(65) Prior Publication Data
US 2006/0229855 A1  Oct. 12, 2006

Related U.S. Application Data

(63) Continuation of application No. 11/068,919, filed on Mar. 2, 2005, now Pat. No. 7,089,165, which is a continuation of application No. 09/813,914, filed on Mar. 22, 2001, now Pat. No. 7,035,777.

(30) Foreign Application Priority Data

Mar. 31, 2000 (JP) .............................. 2000-101188
Sep. 18, 2000 (JP) .............................. 2000-286849

(51) Int. Cl.
*G06G 7/48* (2006.01)
(52) U.S. Cl. .................................. 703/9; 703/2; 703/22
(58) Field of Classification Search ..................... 703/2, 703/9, 22; 376/249; 73/86, 592
See application file for complete search history.

(56) References Cited

U.S. PATENT DOCUMENTS

| 4,779,453 A | 10/1988 | Hopenfeld |
| 4,922,748 A | 5/1990 | Hopenfeld |
| 4,935,195 A * | 6/1990 | Palusamy et al. ........... 376/249 |

FOREIGN PATENT DOCUMENTS

| JP | 08-178172 | 7/1996 |
| JP | 10-141600 | 5/1998 |

OTHER PUBLICATIONS

Miyazaki et al., K. Fracture Behavior of Crabon Steel Pipe with Local Wall Thinning Subjected to Bending Load, Nuclear Engineering and Design, vol. 191, No. 2, Jul. 1999, pp. 195-204.*

(Continued)

*Primary Examiner*—Russell Frejd
(74) *Attorney, Agent, or Firm*—Mattingly, Stanger, Malur & Brundidge, P.C.

(57) ABSTRACT

A wall-thickness thinning rate at a not-measured position is estimated using information having a small number of measured points. Simulation of behavior of fluid flowing inside a pipe line is performed based on wall-thickness data of pips and three-dimensional layout data of the pipe line including the pips using a computer, and simulated wall-thickness thinned data of the pipes composing the pipe line is calculated from change of the simulated behavior of fluid.

1 Claim, 34 Drawing Sheets

OTHER PUBLICATIONS

Ferng et al, "Prediction of Pipe Thinning Location for Nuclear Power Plant and Its Application to Pipe Wall Monitoring", Monthly Journal of Taipower's Engineering, Feb. 1999, vol. 606, pp. 10-27.

Ferng et al, "A Physical Model to Predict Wear Sites Engendered by Flow-Assisted Corrosion", Nuclear Technology, vol. 126, Jun. 1999, pp. 319-330.

Chung et al, "A Study on Wear Locations for HP Turbine Extraction Piping in the Maanshan Nuclear Power Plant", Canadian Nuclear Society, May 1998, pp. 1655-1662.

Kalahasti, S. et al, Performance Characterization of a Novel Flat Plate Micro Heat Pipe Spreader, IEEE Transactions on Components and Packaging Technologies, vol. 25, No. 4, Dec. 2002, pp. 554-560.

Ming, F.Y. et al, "Prediction of Pipe Thinning Location for Nuclear Power Plant and its Application to Pipe Wall Monitoring", Dialog/Inspec., Monthly Journal of Taipowers Engineering, Taiwan Power Co., Feb. 1999, pp. 10-27.

Peng, M.Y. et al, "Influence of Flow Field on Piping Erosion Corrosion and Pipe Wall Monitoring", Dialog/Inspect., Monthly Journal of Taipowers Engineering, Taiwan Power Co., Jan. 1997, pp. 1-20.

Yin, J. et al, "In-Place Detection of Internal and External Corrosion for Undergound Casting Pipes", Proceedings of the IEEE International Conference on Industrial Technology, Dec. 1994, pp. 789-793.

Miyazaki, S. et al, "A Piezo-Electric Pump Driven by a Flexural Progressive Wave", Micro Electro Mechanical Systems, 1991, IEEE, MEMS '91, Jan. 1991, pp. 283-288.

Ferng, Yuh-Ming et al, "Prediction of Pipe Thinning Location for Nuclear Power Plant and Its Application to Pipe Wall Monitoring", Monthly Journal of Taipower's Engineering, Feb. 1999, pp. 10-27 (with English Abstract).

Ferng, Yuh-Ming et al, "A Physical Model to Predict Wear Sites Engendered by Flow-Assisted Corrosion", Nuclear Technology, Jun. 1999, vol. 126, No. 3, pp. 319-330.

Chung, N.M. et al, "A study on Wear Locations for HP Turbine Extraction Piping In the Maanshan Nuclear Power Plant", Canadian Nuclear Society, May 1998, pp. 1655-1662.

European Office Action, EP 01302681, Jul. 31, 2006, pp. 1-8.

* cited by examiner

FIG. 7

| PART ID | KIND OF PART | SHAPE | MATERIAL | ... | SYSTEM No. | PIPE-LINE No. | MEASURED WALL-THICKNESS DATA |
|---|---|---|---|---|---|---|---|
| EQ-001 | EQUIPEMENT | BLOCK(30×100×20) | Fe | ... | | | |
| EQ-002 | | | | ... | | | |
| ... | | ... | ... | ... | | | |
| PIPE-001 | PIPE | CYLINDR(10×60) | Fe | ... | | | |
| PIPE-002 | | ... | ... | ... | | | |

| KIND OF PART | POSITIONAL INFORMATION |
|---|---|
| EQUIPEMENT | CENTER COORDINATE (X, Y, Z) |
| PIPE | END POINT ($X_2$, $Y_2$, $Z_2$) - STARTING POINT ($X_1$, $Y_1$, $Z_1$) |
| ... | ... |

| KIND OF PART | CONNECTION INFORMATION |
|---|---|
| EQUIPEMENT | (CONNECTION PART ID), ... |
| PIPE | (CONNECTION PART $ID_1$), (CONNECTION PART $ID_2$), ... |
| ... | ... |

FIG. 9

| PART ID | FLUID NAME | TEMPERATURE | PRESSURE | DISSOLVED OXYGEN CONCENTRATION | AVERAGE FLOW VELOCITY |
|---|---|---|---|---|---|
| PIPE-001 | STEAM | 170°C | 55Pa | 10ppb | 43 m/s |
| PIPE-002 | LIGHT WATER | 66°C | 6Pa | 3ppb | 15 m/s |
| PIPE-003 | LIGHT WATER | 30°C | 1Pa | 1ppb | 7 m/s |
| .. | .. | .. | .. | .. | .. |

| PART ID | KIND OF PART | SHAPE | MATERIAL | ... | SYSTEM No. | PIPE-LINE No. | MEASURED WALL-THICKNESS DATA |
|---|---|---|---|---|---|---|---|
| PIPE-001 | PIPE | CYLINDER(10×60) | SCPG | | | | 3 |
| PIPE-002 | PIPE | CYLINDER(10×60) | STPT | | | | 9 |
| ... | ... | ... | ... | | | | ... |
| VAL-001 | VALVE | CYLINDER(10×60) | SCPH | | | | 4 |

1801 / 1802

| KIND OF PART | POSITIONAL INFORMATION |
|---|---|
| EQUIPMENT | CENTER COORDINATE (X, Y, Z) |
| EQUIPMENT | END POINT (X2, Y2, Z2) – STARTING POINT (X1, Y1, Z1) |
| ... | ... |

1803

| KIND OF PART | CONNECTION INFORMATION |
|---|---|
| EQUIPMENT | (CONNECTION PART ID), ... |
| PIPE | (CONNECTION PART ID1), (CONNECTION PART ID2), ... |
| ... | ... |

| PIPE ID | LENGTH | REPLACED OBJECT |
|---------|--------|-----------------|
| PIPE-1  | 1200   | 1               |
| PIPE-2  | 2000   | 1               |
| ⋮       | ⋮      | ⋮               |
| VAL-1   | 500    | 1               |
| VAL-2   | 550    | 0               |
| ⋮       | ⋮      | ⋮               |

FIG. 20

| COMBINATION No. | PIPE ID | 0 | 3 | 6 | 9 |
|---|---|---|---|---|---|
| 1 | VAL-1 | 1 | 1 | 1 | 1 |
|   | PIPE-2 | 1 | 1 | 1 | 1 |
| 2 | VAL-1 | 1 | 1 | 1 | 0 |
|   | PIPE-2 | 1 | 1 | 1 | 1 |
| 3 | VAL-1 | 1 | 1 | 1 | 1 |
|   | PIPE-2 | 1 | 1 | 1 | 0 |
| 4 | VAL-1 | 1 | 1 | 1 | 0 |
|   | PIPE-2 | 1 | 1 | 1 | 0 |
| 5 | VAL-1 | 1 | 1 | 1 | 1 |
|   | PIPE-2 | 1 | 1 | 0 | 1 |
| 6 | VAL-1 | 1 | 1 | 1 | 0 |
|   | PIPE-2 | 1 | 1 | 0 | 1 |
| 7 | VAL-1 | 1 | 1 | 1 | 1 |
|   | PIPE-2 | 1 | 1 | 0 | 0 |
| 8 | VAL-1 | 1 | 1 | 1 | 0 |
|   | PIPE-2 | 1 | 1 | 0 | 0 |
| 9 | VAL-1 | 1 | 1 | 1 | 1 |
|   | PIPE-2 | 1 | 0 | 1 | 1 |
| 10 | VAL-1 | 1 | 1 | 1 | 0 |
|    | PIPE-2 | 1 | 0 | 1 | 1 |
| 11 | VAL-1 | 1 | 1 | 1 | 1 |
|    | PIPE-2 | 1 | 0 | 1 | 0 |
| 12 | VAL-1 | 1 | 1 | 1 | 0 |
|    | PIPE-2 | 1 | 0 | 1 | 0 |
| 13 | VAL-1 | 1 | 1 | 1 | 1 |
|    | PIPE-2 | 1 | 0 | 0 | 1 |

FIG. 22

| | SCAFFOLD | ...... | DECONTAMINATION | | ...... | CUTTING | | ...... | DISPOSITION | ...... |
|---|---|---|---|---|---|---|---|---|---|---|
| | SETTING-UP | ...... | REMOVING INSULATOR | INJECTING DECONTAMINANT | ...... | FIXING PIPE | CUTTING PIPE | ...... | CARRYING-OUT | ...... |
| JOB HOURS | 15 | ...... | 8 | 13 | ...... | 11 | 10 | ...... | 3 | |

| | INSTALLING | ...... | WELDING | ...... | PAINTING | ...... |
|---|---|---|---|---|---|---|
| ...... | PLACING PIPE | ...... | BUTTING | ...... | CLEANING | ...... |
| | 12 | | 13 | | 2 | |

FIG. 23

| | SCAFFOLD | | ... | DECONTAMINATION | | ... | CUTTING | | ... | DISPOSITION | |
|---|---|---|---|---|---|---|---|---|---|---|---|
| | SETTING-UP | ... | ... | REMOVING INSULATOR | INJECTING DECONTAMINANT | ... | FIXING PIPE | CUTTING PIPE | ... | ... | CARRYING-OUT |
| PIPE-1 | 1 | | | 1 | 1 | | 1 | 1 | | | |
| PIPE-2 | 1 | | | 1 | 1 | | 1 | 1 | | | |
| ... | | | | | | | | | | | |
| VAL-1 | 1 | | | 0 | 1 | | | | | | 1 |
| VAL-2 | 0 | | | 0 | 0 | | | | | | 1 |

| | INSTALLING | ... | WELDING | ... | PAINTING | ... |
|---|---|---|---|---|---|---|
| | PLACING PIPE | ... | BUTTING | ... | CLEANING | ... |
| | 1 | | 1 | | 1 | |
| | 1 | | 1 | | 1 | |
| ... | | | | | | |
| | 1 | | 1 | | 1 | |
| | 1 | | 1 | | 1 | |

FIG. 25

| B\A | 0 | 1 | 2 | 3 | 4 | 5 | 6 | 7 | 8 | 9 |
|---|---|---|---|---|---|---|---|---|---|---|
| 0 | 0 | 20 | 40 | 60 | 80 | 100 | 120 | 140 | 160 | 180 |
| 1 | 200 | 220 | 240 | 260 | 280 | 300 | 320 | 340 | 360 | 380 |
| 2 | 400 | 420 | 440 | 460 | 480 | 500 | 520 | 540 | 560 | 580 |
| 3 | 600 | 620 | 640 | 660 | 680 | 700 | 720 | 740 | 760 | 780 |
| 4 | 800 | 820 | 840 | 860 | 880 | 900 | 920 | 940 | 960 | 980 |
| 5 | 1000 | 1020 | 1040 | 1060 | 1080 | 1100 | 1120 | 1140 | 1160 | 1180 |
| 6 | 1200 | 1220 | 1240 | 1260 | 1280 | 1300 | 1320 | 1340 | 1360 | 1380 |
| 7 | 1400 | 1420 | 1440 | 1460 | 1480 | 1500 | 1520 | 1540 | 1560 | 1580 |
| 8 | 1600 | 1620 | 1640 | 1660 | 1680 | 1700 | 1720 | 1740 | 1760 | 1780 |
| 9 | 1800 | 1820 | 1840 | 1860 | 1880 | 1900 | 1920 | 1940 | 1960 | 1980 |
| ... | ...... | ...... | ...... | ...... | ...... | ...... | ...... | ...... | ...... | ...... |

(UNIT: HOURS h)

FIG. 28

| PART ID | KIND OF PART | SHAPE | MATERIAL | ····· | WALL THICKNESS | LENGTH | UNIT PRICE |
|---|---|---|---|---|---|---|---|
| PIPE-001 | PIPE | CYLINDER (10×60) | SCPG | | | | 100 |
| PIPE-002 | PIPE | CYLINDER (10×60) | STPT | | | | 150 |
| ······ | ······ | ······ | ······ | | | | ······ |
| VAL-001 | VALVE | CYLINDER (10×60) | SCPH | | | | 300 |

| | SCAFFOLD | | ...... | DECONTAMINATION | | ...... | CUTTING | | ...... | DISPOSITION | ...... |
|---|---|---|---|---|---|---|---|---|---|---|---|
| | SETTING-UP | ...... | | REMOVING INSULATOR | INJECTING DECONTAMINANT | | FIXING PIPE | CUTTING PIPE | | CARRYING-OUT | ...... |
| PIPE-1 | 6 | ...... | ...... | 5 | 24 | ...... | 5 | 5 | ...... | 15 | ...... |
| PIPE-2 | 6 | ...... | ...... | 8 | 0 | ...... | 5 | 5 | ...... | 0 | ...... |
| ...... | | | | | | | | | | | |
| VAL-1 | 6 | ...... | ...... | 0 | 0 | ...... | 12 | 0 | ...... | 0 | ...... |
| TOTAL | 18 | | | 13 | 24 | | 22 | 10 | | 15 | |

⎫ 2901

| | INSTALLING | ...... | WELDING | ...... | PAINTING | | ...... | TOTAL MAN-HOUR |
|---|---|---|---|---|---|---|---|---|
| | PLACING PIPE | | BUTTING | | CLEANING | ...... | | |
| | 10 | ...... | 15 | ...... | 5 | ...... | ...... | |
| | 10 | ...... | 15 | ...... | 5 | ...... | ...... | |
| ...... | | | | | | | | |
| | 12 | ...... | 15 | ...... | 5 | ...... | ...... | |
| TOTAL | 32 | | 45 | | 16 | | | |

⎫ 2901
  2902

2903
| TOTAL OMISSIBLE MAN-HOURS |
|---|
| 35 |

2904
| TOTAL JOB MAN-HOUR BY COMBINING PIPES |
|---|
| |

FIG. 30

| WARK PLAN No. | LOSS OF POWER |
|---|---|
| 1 | 24000 |
| 2 | 21000 |
| 3 | 21000 |
| 4 | 18000 |
| 5 | 19000 |
| 6 | 18000 |
| ⋮ | ⋮ |

FIG. 31

| PIPE ID | TOTAL MATERIAL COST |
|---|---|
| 1 | 800 |
| 2 | 1200 |
| 3 | 2400 |
| ⋮ | ⋮ |
| | 4400 |

FIG. 32

| COMBINATION No. | PIPE ID | 0 | 3 | 6 | 9 | Cost (10 THOUSANDS YEN) |
|---|---|---|---|---|---|---|
| 1 | PIPE-2 | 1 | 1 | 1 | 1 | |
| | VAL-1 | 1 | 1 | 1 | 1 | 35,800 |
| 2 | PIPE-2 | 1 | 1 | 1 | 0 | |
| | VAL-1 | 1 | 1 | 1 | 1 | 34,510 |
| 3 | PIPE-2 | 1 | 1 | 1 | 1 | |
| | VAL-1 | 1 | 1 | 1 | 0 | 34,360 |
| 4 | PIPE-2 | 1 | 1 | 1 | 1 | |
| | VAL-1 | 1 | 1 | 1 | 1 | 31,830 |
| 5 | PIPE-2 | 1 | 1 | 1 | 1 | |
| | VAL-1 | 1 | 1 | 0 | 1 | 34,360 |
| 6 | PIPE-2 | 1 | 1 | 1 | 0 | |
| | VAL-1 | 1 | 1 | 0 | 1 | 33,070 |
| 7 | PIPE-2 | 1 | 1 | 1 | 1 | |
| | VAL-1 | 1 | 1 | 0 | 0 | 32,920 |
| 8 | PIPE-2 | 1 | 1 | 1 | 0 | |
| | VAL-1 | 1 | 1 | 0 | 0 | 31,630 |
| 9 | PIPE-2 | 1 | 1 | 1 | 1 | |
| | VAL-1 | 1 | 0 | 1 | 1 | 34,360 |
| 10 | PIPE-2 | 1 | 1 | 1 | 0 | |
| | VAL-1 | 1 | 0 | 1 | 1 | 33,070 |
| 11 | PIPE-2 | 1 | 1 | 1 | 1 | |
| | VAL-1 | 1 | 0 | 1 | 0 | 32,920 |
| 12 | PIPE-2 | 1 | 1 | 1 | 0 | |
| | VAL-1 | 1 | 0 | 1 | 0 | 31,630 |
| 13 | PIPE-2 | 1 | 1 | 1 | 1 | |
| | VAL-1 | 1 | 0 | 0 | 1 | 32,920 |

| ... | SCAFFOLD | | ... | DECONTAMINATION | | ... | CUTTING | | ... | DISPOSITION | ... |
|---|---|---|---|---|---|---|---|---|---|---|---|
| | SETTING-UP | ... | | REMOVING INSULATOR | INJECTING DECONTAMINANT | ... | FIXING PIPE | CUTTING PIPE | ... | CARRYING-OUT | ... |
| JOB HOURS | 5 | | | 5 | 0 | | 5 | 5 | | 7 | |

| ... | INSTALLING | ... | WELDING | ... | PAINTING | ... | TOTAL MAN-HOUR |
|---|---|---|---|---|---|---|---|
| | PLACING PIPE | ... | BUTTING | ... | CLEANING | ... | |
| | 5 | | 12 | | 5 | | |

3502

| NUMBER OF OMISSIBLE SECTIONS S |
|---|
| 0 |

METHOD OF OFFERING WALL-THICKNESS THINNING PREDICTION INFORMATION, AND COMPUTER-READABLE RECORDING MEDIUM STORING WALL-THICKNESS THINNING PREDICTION PROGRAM, AND METHOD OF PLANNING PIPING WORK PLAN

This is a continuation application of U.S. Ser. No. 11/068,919, filed Mar. 2, 2005 (now U.S. Pat. No. 7,089,165), which is a continuation application of U.S. Ser. No. 09/813,914, filed Mar. 22, 2001 (now U.S. Pat. No. 7,035,777).

BACKGROUND OF THE INVENTION

1. Field to which the Invention Belongs

The present invention relates to a technology of estimating lifetime of piping parts in a process plant, and a technology of forming a replacing work plan of piping parts using a result of the lifetime estimation.

2. Prior Arts

As disclosed in Japanese Application Patent Laid-Open Publication No. Hei 8-178172 titled "a method of calculating and evaluating wall-thickness thinning of a component and piping system caused by erosion-corrosion" and U.S. Pat. No. 4,935,195 titled "corrosion-erosion trend monitoring and diagnostic system", a conventional maintenance form of a process plant is that a maximum progressed value of pipe wall-thickness thinning for each of the piping parts is predicted by forming a wall-thickness estimation formula using various kinds of information necessary for wall-thickness control, particularly a wall-thickness measurement database and a document database (temperature, pressure, dissolved oxygen concentration, flow speed of the fluid flowing inside the pipe). Further, an inspection plan and a replacing work plan are made for each of the estimated piping parts.

In the conventional technology, by focusing only on an individual piping part such as one elbow or one straight pipe, the wall-thickness thinning prediction has been performed based on past wall-thickness thinning measured data. However, neither of the three-dimensional layout of the part nor the kind and the shape of a part adjacently connected to the part has been taken into consideration.

Because the piping parts (piping (elbow, straight pipe, reducing pipe, branch pipe and so on), valve, pump and so on) composing a process plant are disposed differently in three-dimension even if they are the same kind of parts, have the same shape and are made of the material, behavior of the fluid flowing through the parts is substantially different depending on a position where the parts are disposed and on a kind of a part to which the part is connected.

Therefore, The wall-thickness thinning rate of the piping part is varied depending on the behavior of the fluid flow. Further, durability of a plant part composing the process plant is different depending on the three-dimensional layout of the plant part and on a kind of a part to which the plant part is connected, and also depending on a condition of the fluid flowing inside the plant part and on number of plant shutdowns.

Therefore, the prior art can not have performed wall-thickness thinning prediction which takes into consideration change in the behavior of the fluid flowing through the whole pipe lines composing the process plant, and can not make an efficient plan for-replacing the piping parts based on the prediction result.

Further, the prior art can not have performed wall-thickness thinning prediction on a unmeasured part even within one pipe, and can not have performed lifetime prediction of piping parts and wall-thickness thinning prediction of piping parts composing the whole process plant.

Further, in a conventional plan of replacing parts, in a case where replacing periods of the piping parts are different from one another, the piping part replacing work must be frequently performed for the replacing work corresponding to each of the piping parts. Accordingly, since each time of the replacing work needs preparation associated to the work and shutdown of the plant operation, an economical loss caused by a large cost spent in the preparation and reduction of operability associated with the plant shutdown if the repairing work often occurs.

This is caused by that lifetime of piping parts of the whole process plant has not been accurately known when the replacing work plan using lifetime estimation and wall-thickness thinning estimation of parts such as pipes composing the process plant is made.

SUMMARY OF THE INVENTION

An object of the present invention is to perform a highly accurate wall-thickness thinning prediction.

Another object of the present invention is to make it possible to perform a wall-thickness thinning prediction of a piping part different from a piping part of which the wall-thickness thinning value is not measured.

A further object of the present invention is to provide the estimated wall-thickness obtained as described above to a client.

Further, another object of the present invention is to make it possible to plan a replacing work plan which taking into consideration lifetime and estimated thinned wall-thickness of each of parts composing the whole pipeline or the whole process plant from the above-described estimated results, and to provide estimated wall-thickness obtained as described above to a client.

Further, another object of the present invention is to make it possible to plan an economical replacing work plan for purpose of long term operation by reducing number of times of replacing work for the piping parts of the whole process plant.

Furthermore, another object of the present invention is to make it possible to plan a low-cost and long term plant maintenance plan taking into consideration cost required for the work as well as simply reducing the number of times of replacing the piping parts.

A further object of the present invention is to provide the replacing work plan obtained as described above to a client.

A feature of the present invention is as follows.

Initially, wall-thickness data of piping parts of an objective process plant is measured, or measured results of wall-thickness data are received from a client, and the data is stored in a DB (database).

Fluid data in the piping of the process plant expressing an initial condition of the fluid flowing in the pipe line and three-dimensional layout data of the piping parts are measured or measured received from a client, and the data is pre-stored in a DB.

Next, layout of the piping parts and wall-thickness and shape of each of the piping parts are obtained from the three-dimensional layout data of piping parts.

An amount of thinned wall-thickness is calculated from the thickness obtained from the three-dimensional layout data and the measured thickness data, and a wall-thickness thinning rate per unit time is calculated from a used time of the piping line and the obtained amount of thinned wall-thickness.

Behavior of fluid flowing in the piping part is estimated from a pattern of the wall-thickness thinning rate or the amount of thinned wall-thickness.

Swirl flow data of the fluid flowing the whole pipe line including the piping part is calculated from the behavior of fluid flowing in the piping part and the initial condition shown by the fluid data.

Shear stress values in various positions of the pipe line by performing fluid simulation based on the swirl flow data.

A ratio of a wall-thickness thinning at a wall-thickness measured position to a shear stress at the wall-thickness measured position among the calculated shear stress values is obtained. In detail, the ratio of a wall-thickness thinning per unit shear stress is calculated by dividing a wall-thickness thinning rate by a shear stress.

An estimated wall-thickness value in each position of the pipe line can be calculated by multiplying the ratio of a wall-thickness thinning per unit shear stress to a shear stress in each position of the pipe line.

If a pipe line has no measured position, a shear stress of swirl flow flowing through the pipe line. If there is a pipe line similar to the pipe line, an estimated wall-thickness of the pipe line is calculated using a wall-thickness thinning ratio at the wall-thickness measured position to the shear stress at the wall-thickness measured position of the similar pipe line.

If the is no similar pipe line, an estimated wall-thickness of the pipe line is calculated by setting a wall-thickness thinning ratio at a position having the maximum shear stress as an average value of wall-thickness thinning ratio at the wall-thickness measured position to the shear stress at the wall-thickness measured position of the pipe line of which the wall-thickness has been measured.

In the present invention, since simulation of the behavior of the fluid flowing in the pipe line and the wall-thickness thinning caused by the behavior of the fluid is performed as described above, the wall-thickness thinning not only of the piping parts of which the wall-thickness values are measured, but also of the piping parts of the whole pipe line can be estimated.

Further, by making a work plan for replacing the piping parts based on the estimated wall-thickness thinning results including the estimated wall-thickness thinning results other than the piping parts of which the wall-thickness values are measured, the piping parts to be replaced at the same period can be specified. Therefore, an efficient replacing work plan (a replacing work plan capable of suppressing number of plant shutdown times) of the piping parts in the whole pipe line can be made.

Furthermore, by forming combination of the piping parts capable of reducing the total work cost by performing replacing work at a time in a database, the cost required for the one time of the replacing work can be suppressed by making the replacing work plan using the combination stored in the database.

BRIEF DESCRIPTION OF DRAWINGS

FIG. 7 is a table showing three-dimensional layout information;

FIG. 9 is a table showing in-pipe fluid data;

FIG. 18 is a table showing three-dimensional piping information;

FIG. 20 is a table showing replacing timing plan data;

FIG. 22 is a table showing job hour data;

FIG. 23 is a table showing job procedure data;

FIG. 25 is a job man-hour vs. non-operational period table;

FIG. 28 is a material cost table;

FIG. 29 is a job man-hour data table;

FIG. 30 is a table showing electric power loss data;

FIG. 31 is a table showing total material cost data;

FIG. 32 is a table showing total cost data;

FIG. 35 is a table showing omissible job data; and

DESCRIPTION OF PREFERRED
EMBODIMENTS OF THE INVENTION

Initially, description will be made on a design of a process plant.

Designing of a process plant is generally performed by initially determining positions of installing large components, and then performing logical design connecting between the large components so as to satisfy the target function. This is generally called as system design. For example, in a case of performing logical design of generating steam, an apparatus for making water to a high temperature and high pressure state is initially connected to a steam generator for extracting steam with piping, and after generating the steam, a logical diagram transporting the steam to a turbine blade rotary apparatus with piping is formed.

Therein, pipes made of materials having a function capable of withstanding high pressure and having high heat insulation property are selected and arranged from the apparatus for making water to a high temperature and high pressure state to the steam generator, and piping parts gradually reducing the diameter of the piping are selected and arranged from the steam generator to the turbine blades in order to increase the steam velocity. System design in process plant is to determine arrangement of the piping parts between the plant components such as the steam generator and the steam turbine, as described above.

When the system design is performed, a minimum unit performing the logical design for the identical purpose is called as one piping system.

Further, the piping system is usually composed of a plurality of pipes, not a single pipe, in taking the steam generation efficiency into consideration. A line number of each of the pipes is set as an identifier. That is, one piping system is composed of a plurality of pipes each having an individual line number.

Further, layout design for spatially disposing the logically designed piping is performed. The layout is performed line-number by line-number.

Further, installation work is performed by pre-dividing the pipe in a length of 1.5 m to 2.0 m to be brought in and then joining the pipe sections by welding or the like so as to make the construction and installation easy. This minimum unit of pipe is called as a piping part.

Next, a feature when the present invention is embodied will be described below in detail.

Figure 1:
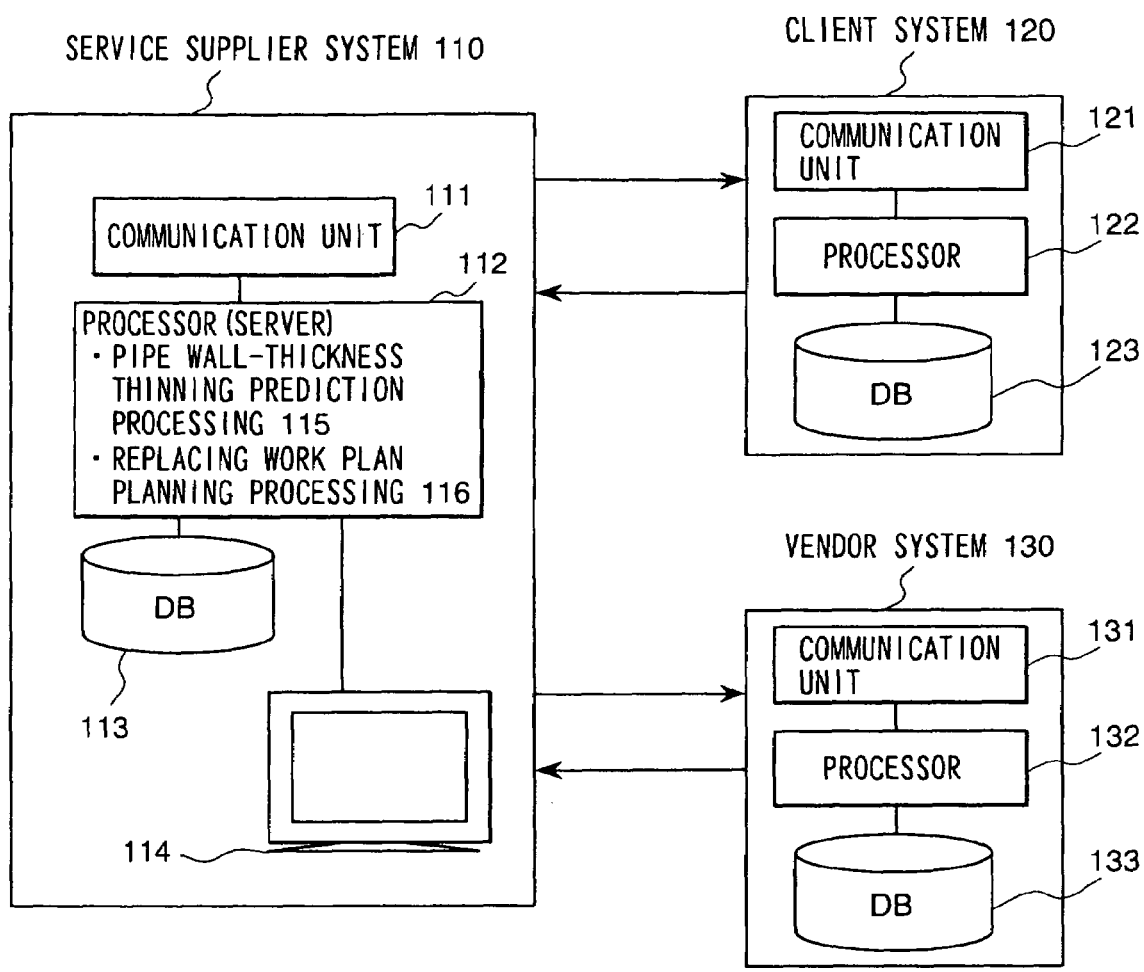
FIG. 1 is a block diagram showing the configuration of a service supplier system in which the present invention is used.

FIG. 1 is a block diagram showing the total system in which the present invention is used.

The present system is composed of a service supplier system 110, a client system 120 and a vendor system 130.

The client system 120 comprises a communication unit 121 connected to the service supplier system with a communication line; a DB 123 storing three-dimensional layout data on piping parts composing the plant, wall-thickness measurement data obtained by measuring wall-thickness of the pipes and in-pipe fluid data on fluid flowing the pipes; and a information processor 122 for performing processing to send the data in the DB 123 through the communication unit and processing to receiving information from the service supplier system 110.

The construction of the vendor system 130 is similar to that of the client system 120.

The service supplier system 110 is composed of a communication unit 111 for performing communication with the client system 120 and the vendor system 130; a database 113; a display unit 114; and an information processor 112 for performing main processing of the service supplier system, the information processor being connected to the communication unit 111 and the database 113 and the display unit 113 and an input units such as a keyboard and so on.

As processing to be executed by the information processor 112, There are pipe wall-thickness thinning prediction processing 115 and replacing work plan planing processing 116. These are processed by executing programs on OS, and these programs are installed programs stored in a recording media or installed by being downloaded through the Internet to the information processor 112.

Figure 2:
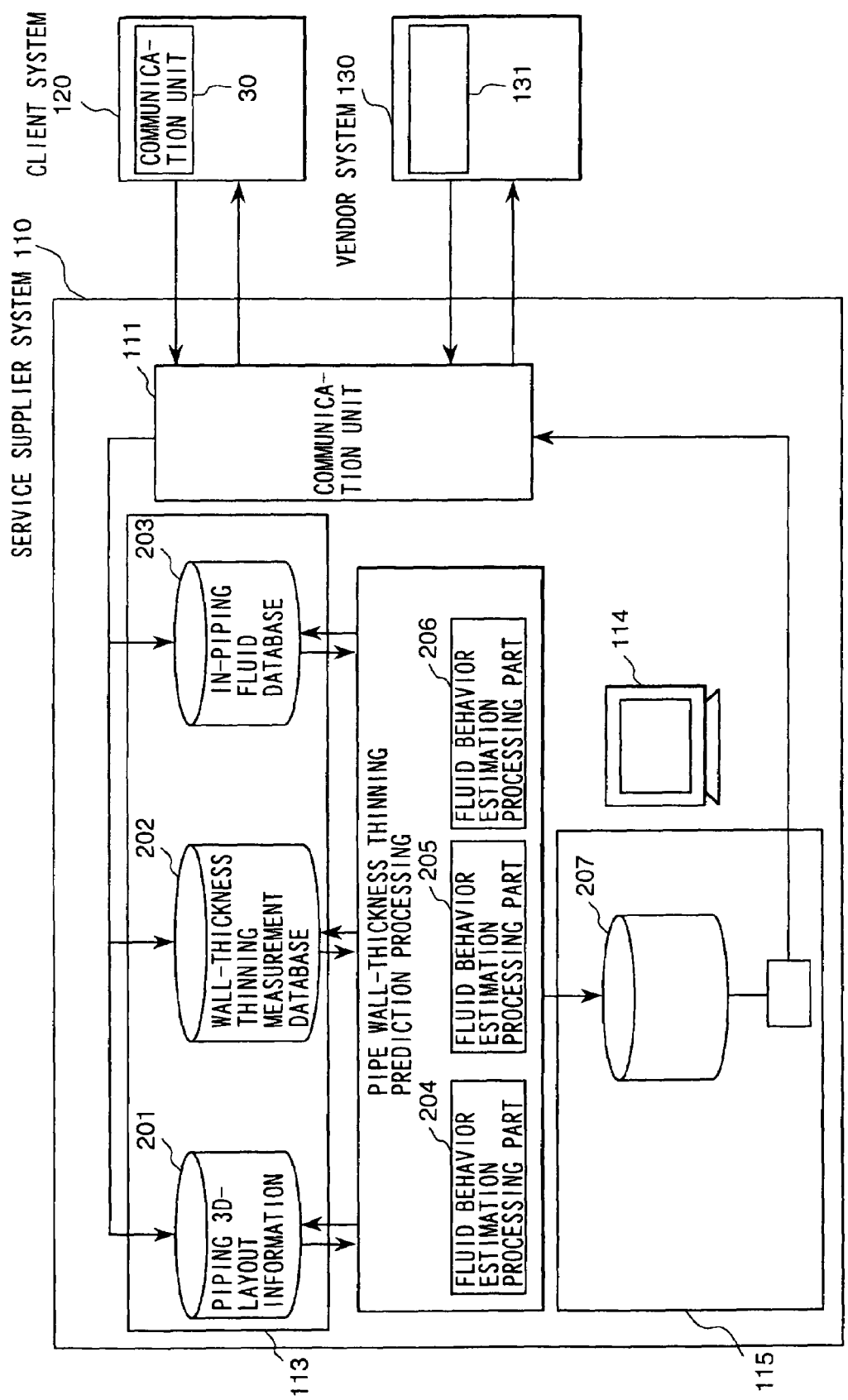
FIG. 2 is a detailed block diagram showing the service supplier system.

FIG. 2 is a detailed block diagram showing the service supplier system.

Figure 8:
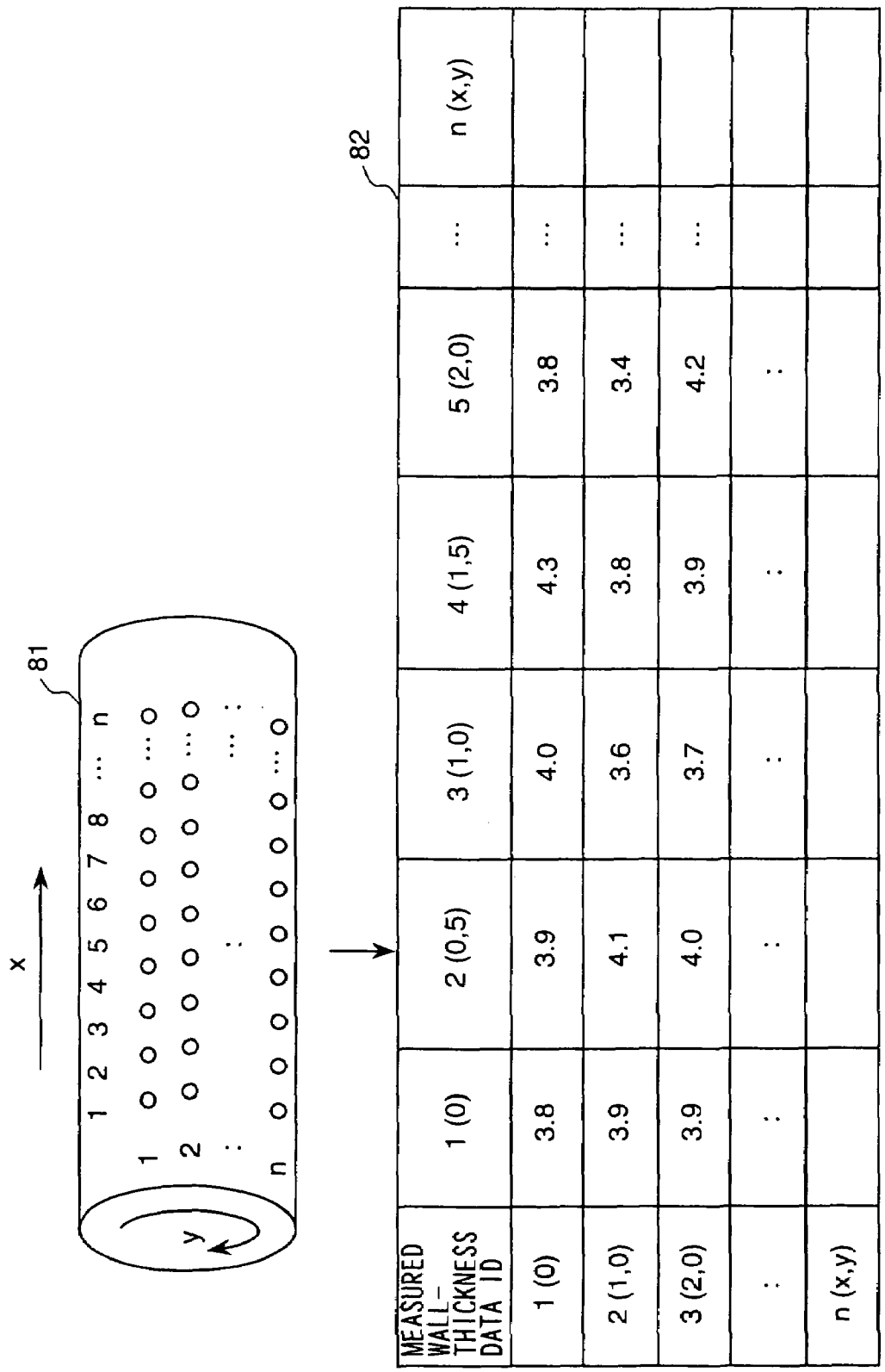
FIG. 8 is a table showing wall-thickness measurement data.

The DB 113 is composed of a database 201 storing the three-dimensional layout information (FIG. 7) of the piping parts; a database 202 storing measured data (FIG. 8) of measured wall-thickness of the piping parts; and a database 203 storing data in regard to fluid flowing inside the pipes (in detail, kind of fluid, average flow velocity, pressure, temperature, oxygen ion concentration, metal ion concentration: FIG. 9) is recorded.

A pipe wall-thickness thinning prediction system 115 for predicting wall-thickness thinning of the pipe line by reading in the wall-thickness prediction program stored in a recording medium is composed of a fluid behavior estimation processing part 241; a fluid simulation processing part 242; an input fluid data generation processing part 243 for generating fluid data at a position near the inlet position of the piping part; and a selection output part 207 for selecting and outputting a position having a high pipe wall-thickness thinning rate.

The selection output part 207 performs processing not only for displaying on the display unit 114, but also for sending the client system 120 through the communication units 111 and 121 and for sending the vendor system 130 through the communication units 111 and 131.

Figure 3:
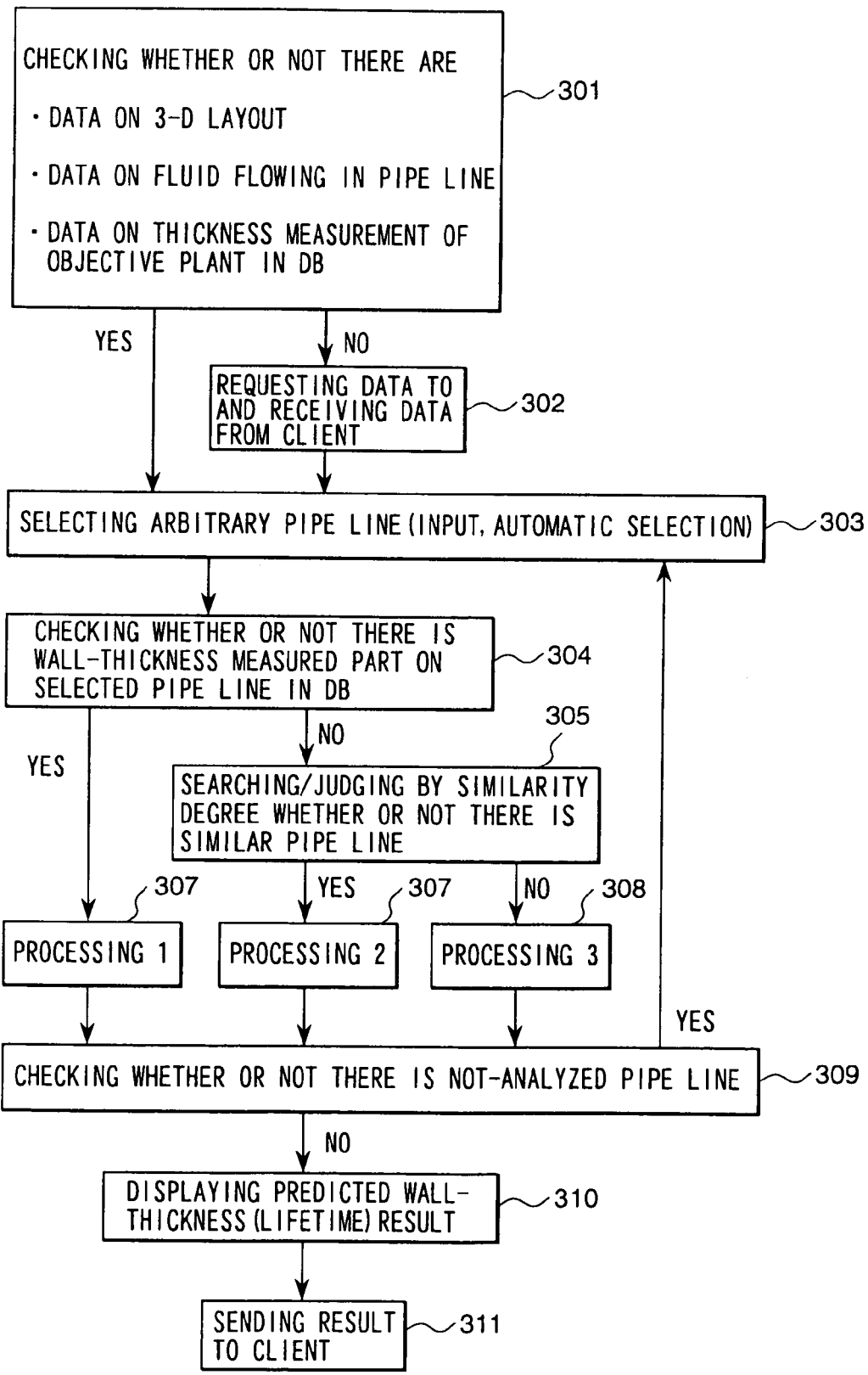
FIG. 3 is a flow diagram of a pipe wall-thickness thinning estimation process.

The replacing work plan planing processing 116 is to be explained later. Initially, the processing of the pipe wall-thickness thinning prediction processing 115 will be described below, referring to FIG. 3.

The processing is performed initially by searching and checking whether or not there are three-dimensional layout data on pipes of an objective plant, fluid data on fluid flowing in the pipe line and wall-thickness measured data (Process 3). If not, the data is received by requesting the data to the client system 120 through the communication unit 120 (Process 302).

Next, as a piping part ID is input from the keyboard or the mouse 94, the piping part ID is directly input to the fluid simulation processing part 205 (through the communication units 111 and 121). The fluid simulation processing part 205 reads the piping three-dimensional layout information of the piping of the objective plant from the DB 201, and selects a pipe line including the input piping part ID, and searches piping parts contained in the pipe line using the part ID as the key (Process 303).

Therein, the piping three-dimensional information of the DB 202 is managed the piping based on part ID, position information, connection information, shape, material, system number, pipe line number and measured wall-thickness data ID. Therefore, the input piping part ID can be used as a key to search the corresponding pipe line number, and the pipe line number can be further used as a key to search the part ID included in the pipe line.

Next, based on the piping part ID of the wall-thickness measured data of the DB 202, it is judged based on presence or absence of the measured wall thickness data number in the piping three-dimensional layout information whether or not the pipe line including the selected pipe part includes any piping part of which wall-thickness thinning value has been measured (Process 304).

If the check result is that there is a piping part of which wall-thickness thinning value has been measured on the pipe line, Processing 1 is executed.

If there is no piping part of which wall-thickness thinning value has been measured on the pipe line, it is checked whether or not there is any similar pipe line (Process 305).

The similarity here is judged by that the pipe line is in the same system, and that the diameter of the pipe and the average velocity of fluid flowing in the pipe are within a certain range.

If there is any similar pipe line, Processing 2 is executed. If there is no similar pipe line, Processing 3 is executed. Therein, Processing 1 to Processing 3 are for calculating estimated wall-thickness of a selected pipe line using data stored in the DBs 201 to 203.

After executing processing 1 to 3, it is checked whether or nor there is any still-not-analyzed pipe line (Process 309).

If there is any still-not-analyzed pipe line, the processing is returned to Process 302. If not, the processing proceeds to the next Process 310.

After completing all of the pipe lines, the estimated wall-thickness result is displayed.

At that time, in the selection output part, a piping part having a wall-thickness value thinner than a preset value is displayed on the display unit 114 by changing color in order to enhancement (Process 310).

After that, the result is sent to the client, and the replacing work plan planning processing 116 is to be executed.

The Processing 1 to Processing 3 described above will be described below.

Initially, the data stored in the DBs 201 to 203 are read.

Figure 4:
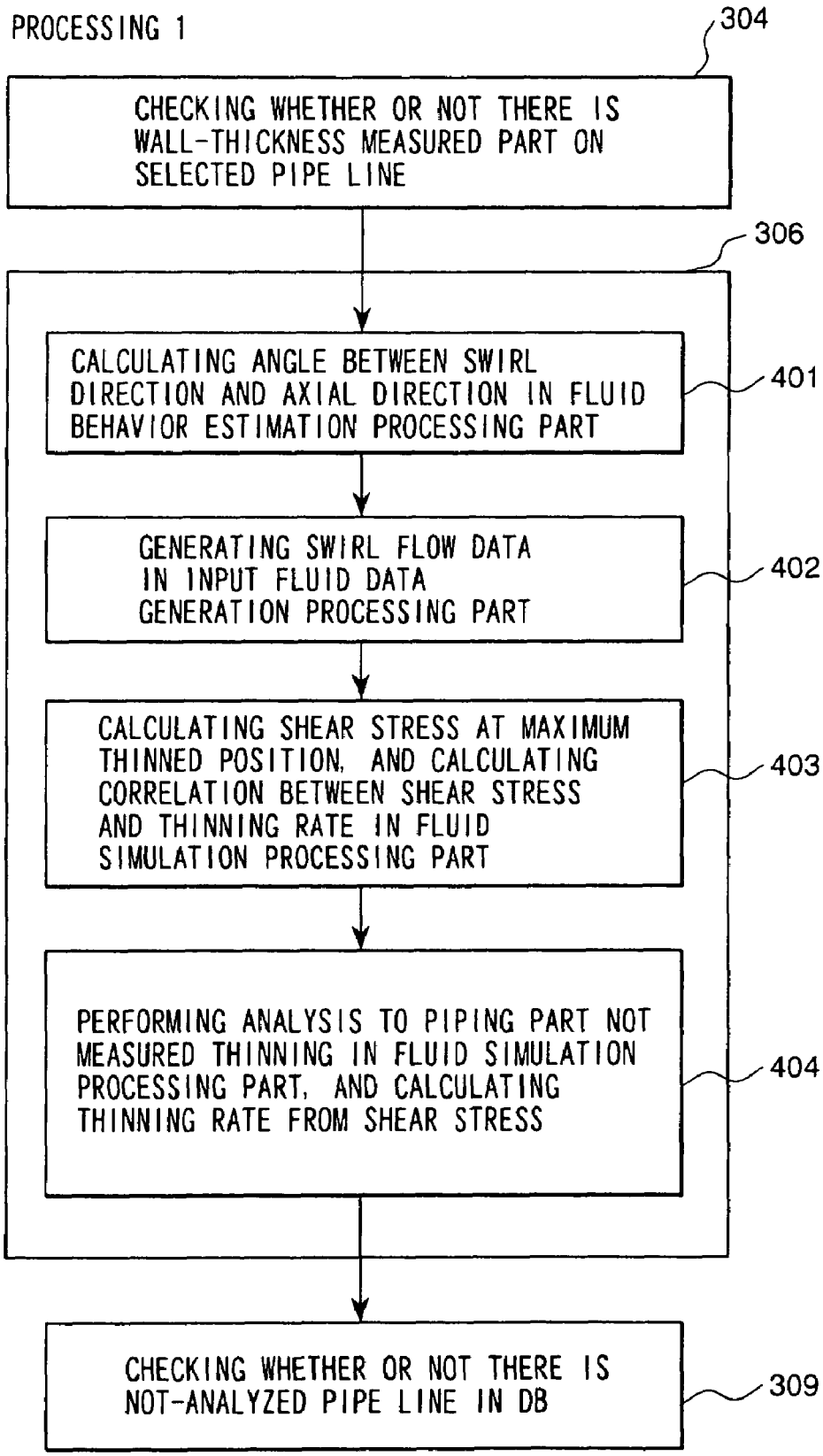
FIG. 4 is a flow diagram of Process 1.

FIG. 4 is a flowchart showing the outline of Processing 1.

Figure 10:
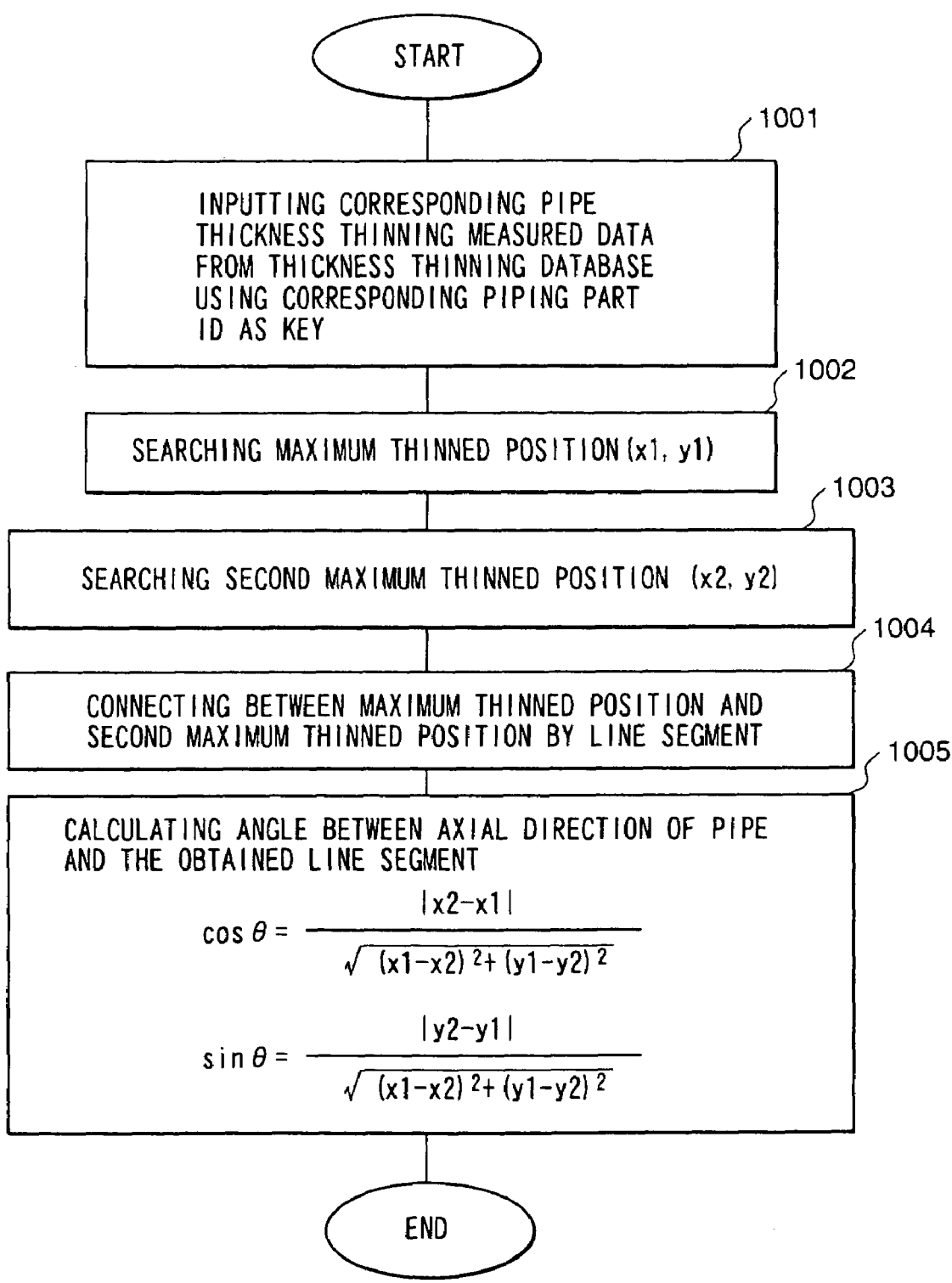
FIG. 10 is a flowchart showing a fluid behavior estimation processing part.

Firstly, in the fluid behavior estimation part 204, a swirl direction of the fluid flowing in the pipe and an axial direction are obtained (Process 401). This process 401 is performed according to the flow shown in FIG. 10.

The wall-thickness measurement data contained in the selected pipe line is selected out of the wall-thickness measurement database 202 using the corresponding measured wall-thickness data ID as the key (Process 1001). Next, the maximum and the second maximum wall-thickness thinned positions among the measured wall-thickness data are searched from the input wall-thickness thinned position data (Processes 1002, 1003).

The maximum wall-thickness thinned position is connected to the second maximum wall-thickness thinned position with a line segment (Process 1004), and an angle of the line segment to the axial direction of the pipe is calculated (Process 1005). This obtained angle is let to be the swirl flow of the fluid at a position near the piping part of which the thickness is measured.

Next, swirl flow data is generated in the fluid data generating part (Process 402).

Figure 12:
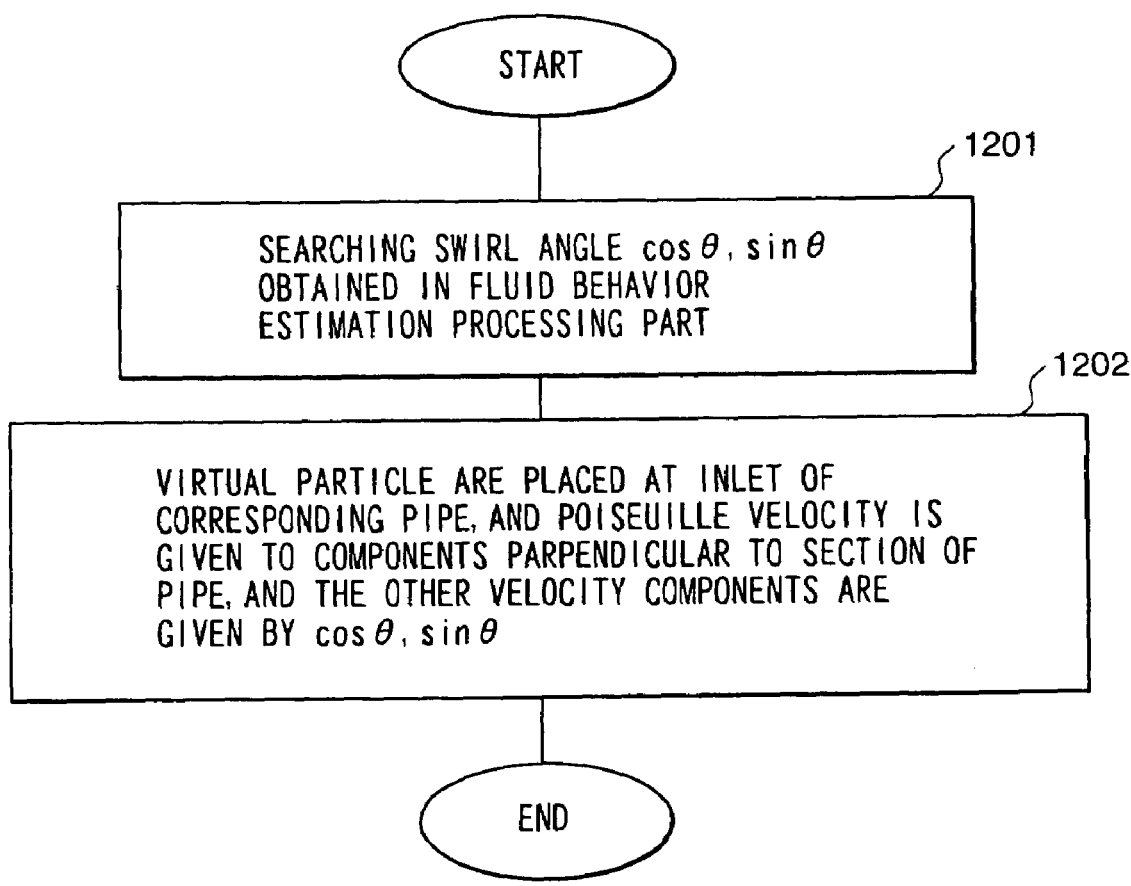
FIG. 12 is a flowchart showing an input fluid data generation processing part.
Figure 13:
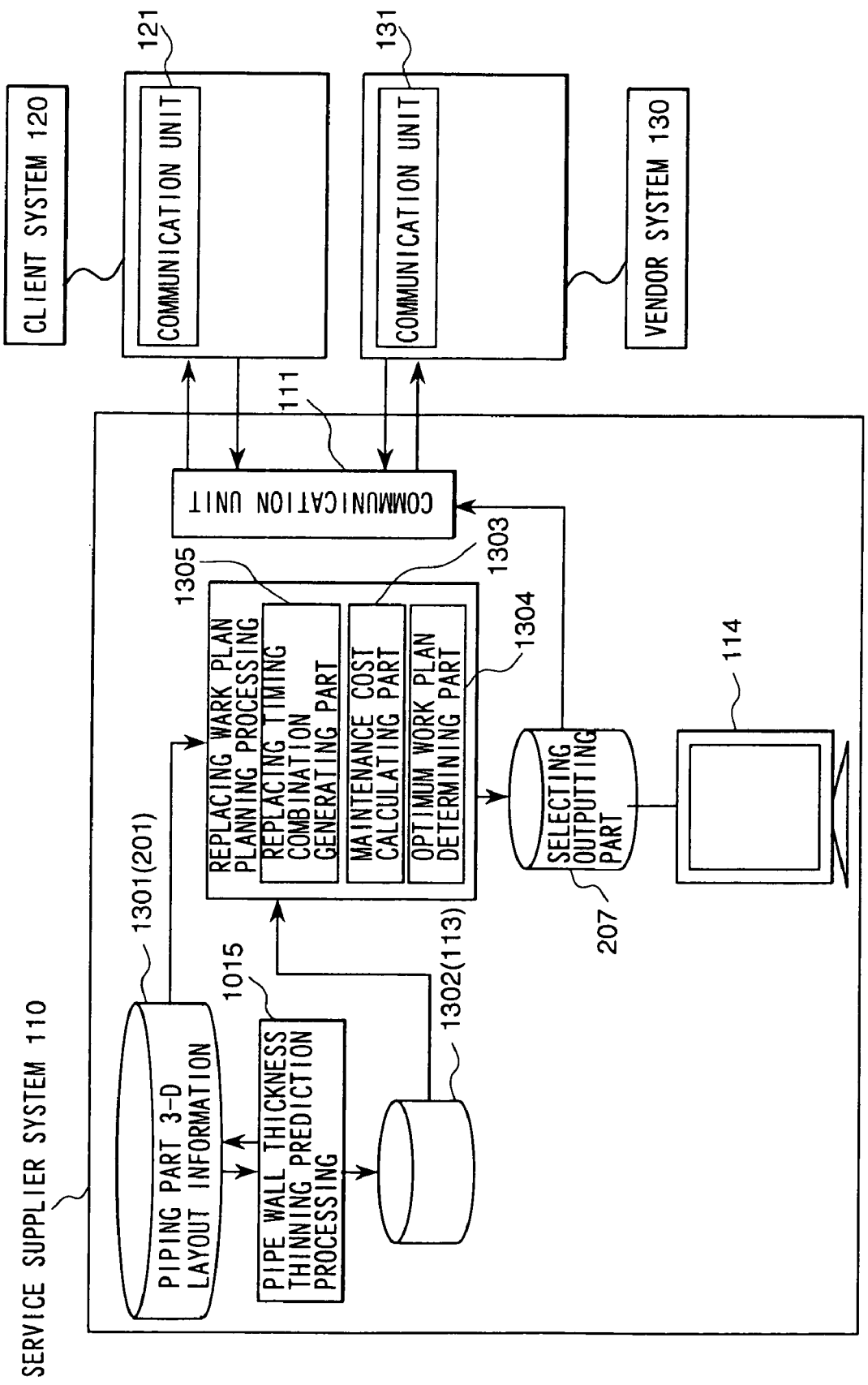
FIG. 13 is a detailed block diagram showing the replacing work plan planning processing.

As shown in FIG. 12, the swirl angle $\cos\theta$, $\sin\theta$ obtained in the fluid behavior estimation processing part is searched (Process 1201), and virtual particles are aligned in the inlet of the pipe, and Poiseuille flow velocity is given to in the vertical direction of the cross section of the pipe, and the other velocity components are given by $\cos\theta$, $\sin\theta$.

Figure 11:
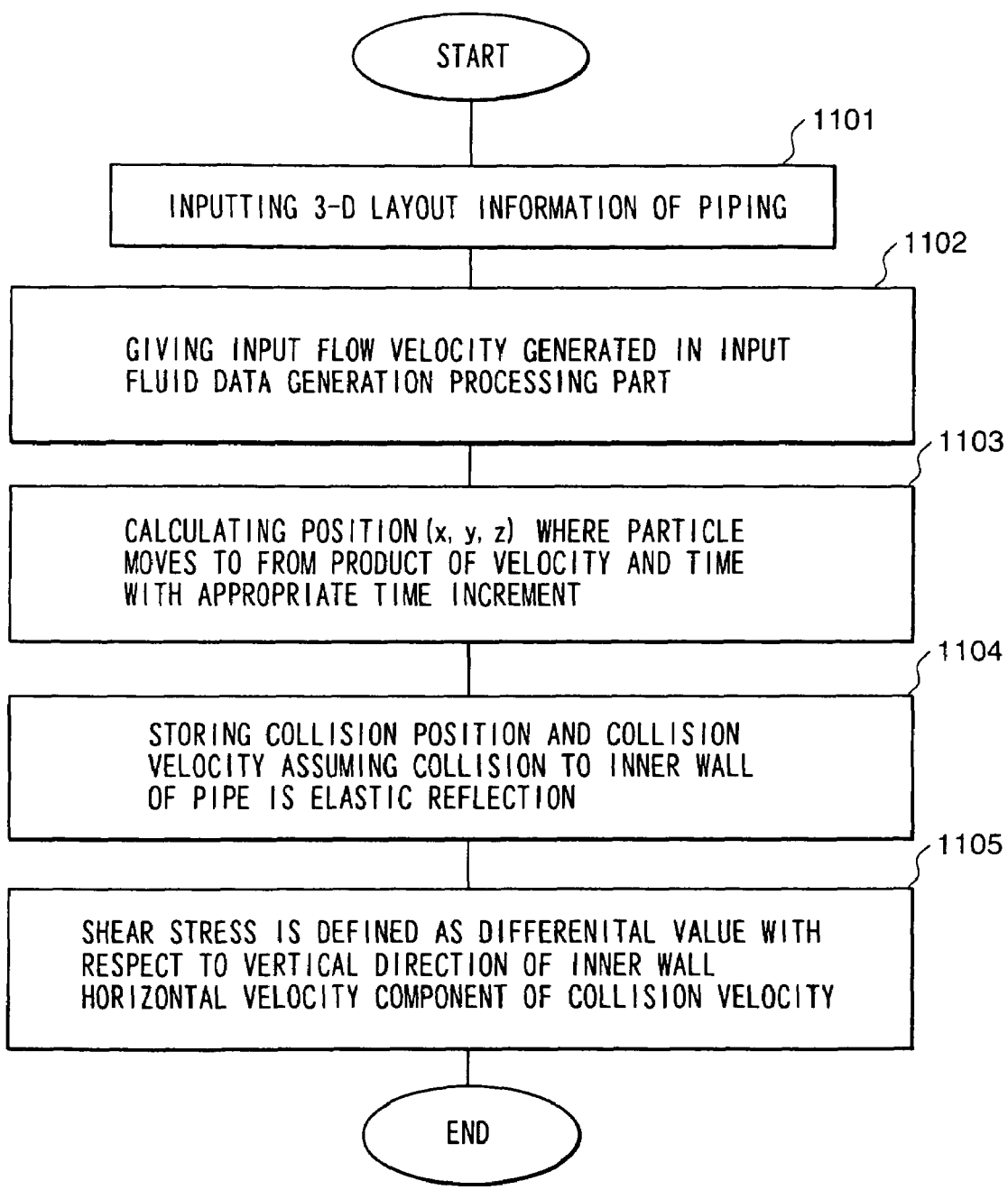
FIG. 11 is a flowchart showing a fluid simulation processing part.

Further, in the fluid simulation processing 242, a shear stress at the maximum wall-thickness thinning position is calculated to obtain the wall-thickness thinning rate per unit shear stress (Process 403). The processing flow shown in FIG. 11 is used for performing these processes. That is, the three-dimensional layout information of the pipe on the pipe length and the pipe diameter is retrieved from the DB 201.

Then, the average velocity and the viscosity of the fluid are read from the in-pipe fluid database 203 using the piping part ID as the key. The pipe length, the pipe diameter, the average velocity and the viscosity read are substituted into individual terms of Equation 3 to calculate the velocity distribution in the piping part, and a shear stress is calculated by differentiating the velocity with respect to the normal component of the inner wall surface and by multiplying a constant determined by the viscosity, as shown by Equation 4.

Next, the wall-thickness measured data is retrieved from the DB 202, and an amount of wall-thickness thinning is calculated by subtracting the wall-thickness from the wall-thickness data value stored in the three-dimensional layout data, and a wall-thickness thinning rate is calculated by dividing the amount of all-thickness thinning by the use period of the pipe. Then, a wall-thickness thinning rate per unit shear stress is calculated by dividing the wall-thickness thinning rate by the obtained shear stress.

$$V = \frac{\Delta p}{4\eta l}(R^2 - r^2)(l, \cos\theta, \sin\theta) \qquad \text{(Equation 3)}$$

$$\sigma = k\frac{\delta V}{\delta y} \qquad \text{(Equation 4)}$$

There, $\sigma$ is a shear stress, k is a constant, and y is a component normal to the inner wall.

Analysis is performed to the piping parts of which the wall-thickness values are not measured, on the pipe line in the fluid simulation processing part in order to calculate shear stresses acting on individual piping parts.

The wall-thickness thinning rate for each of the piping parts is calculated by multiplying the wall-thickness thinning rate per unit shear stress to the shear stress for each of the piping parts, as shown by Equation 5 (Process 404)

$$S = \sigma \frac{S_l}{\sigma_l} \qquad \text{(Equation 5)}$$

There, $S_1$ is the wall-thickness thinning rate at the maximum measured wall-thickness thinned position, and $\sigma_1$ is the shear stress at the maximum measured wall-thickness thinned position. An estimated wall-thickness in the future is calculated by multiplying a period to the wall-thickness thinning rate.

In the fluid simulation processing part 205, the fluid analysis is executed through the method that the fluid behavior is expressed by particles and paths of the particles are traced by calculating the motion of the particles in the three-dimensional pipe by the product of the velocity and the elapsed time. At that time, the swirl angle (direction) obtained by the fluid behavior estimation part is searched (Process 1201).

Virtual particles are aligned in the inlet of the corresponding pipe, and Poiseuille flow velocity is given to in the vertical direction of the cross section of the pipe, and the other velocity components are given by $\cos\theta$, $\sin\theta$, and the searched swirl angle is substituted into the $\theta$. Then, when the particle collide against the inner wall of the pipe, the particle is elastically reflected and the collision position (coordinate values) is output. The shear stress is identified the velocity of the collision particle and number of collisions per unit time and per unit area.

Here, description will be made on that the swirl flow is used in the fluid simulation, referring to Equation 3.

The velocity of the fluid flowing in the pipe is fast at a position distant from the inner wall of the pipe due to the effect of a viscous force acting on the inner wall of the pipe. The motion of the fluid can be expressed by the partial differential equation called as Navier-Stokes equation.

$$\frac{\delta V}{\delta t} + (V \cdot \text{grad})v = -\frac{1}{\rho}\text{grad}p + \frac{\eta}{\rho}\nabla^2 V \qquad \text{(Equation 1)}$$

There, V is a velocity vector, t is time, v is a velocity, $\rho$ is a density, p is a pressure, and $\eta$ is a viscosity.

That is, the equation of motion can be expressed by the sum of the advection term expressing the effect of flicking out the surrounding fluid particles by an inertia force of the fluid; the diffusion term expressing the effect of retarding the speed of the surrounding fluid particles by an intermolecular force; and the pressure gradient term expressing the effect of giving a forward moving force to the fluid particles.

Although the motion of the fluid is unstable because the advection term expressing the effect of flicking out the fluid particles is non-linear, the diffusion term acts so as to stabilize the flow. Therefore, the magnitude of the diffusion term strongly affect the whole behavior of the fluid.

Since the boundary of the flow in the pipe is enclosed with the pipe, the constraint is strong and accordingly the flow is stabilized compared to a flow in an open space. An ideal flow in the pipe is of a quadratic parabolic flow distribution called as Poiseuille flow.

As a solution of Navier-Stokes equation satisfying the Poiseuille flow, there is Equation 2.

$$v = \frac{\Delta p}{4\eta l}(R^2 - r^2) \quad \text{(Equation 2)}$$

There, l is a length of the pipe, R is a radius of the pipe, and r is a distance form the center of the pipe.

However, since the section of the pipe is circular, the velocity distribution is symmetrical. The velocity is mathematically stable, but physically unstable. An example of the evidence is that a ball of baseball flies on a more stable path when the ball is rotated.

Since the boundary of the flow is surrounded by the inner wall of the pipe, the flow distribution rarely becomes the ideal Poiseuille flow having symmetry, but the inside flow becomes a stable swirl-dominant flow. Therefore, it is assumed that the swirl flow is the quadratic parabolic flow distribution of Poiseuille flow which is rotating in the circumferential direction of the pipe, and accordingly it has decided that the rotating angle is determined from the wall-thickness thinning tendency of the measured pipe.

Therefore, Equation 2 is converted to Equation 3.

Although small fluctuations in the fluid velocity actually occur everywhere, the main factor of the shear stress to cause corrosion fatigue in the inner wall of the pipe is the swirl flow which is a main component of the fluid flow. This is because the main factor of the shear stress to cause corrosion fatigue in the inner wall of the pipe is an impact force of the fluid against the inner wall of the pipe.

A stable oxide film (this is called as a passive film) is formed on the metal surface, but after initiation of the plant operation, the passive film is peeled off by the impact force of the fluid flowing inside the pipe. Because the metal is directly exposed to the fluid at the position where the passive film is peeled, both of an anode reaction of dissolving metallic ions into the fluid and a reaction of forming the passive film occur at a time.

On the other hand, a chemical reaction of consuming electrons on the passive film occurs as a cathode reaction. When the anode reaction of dissolving the metal ions is dominant to the reaction of forming the passive film, a phenomenon of progressing corrosion called as wall-thickness thinning occurs.

On the contrary, when the reaction of forming the passive film is dominant, corrosion progresses from a point on the surface to the inside of the metal to cause a corrosion crack. The both kinds of corrosions can be predicted if the peeling-off positions of the passive film can be identified from the fluid behavior.

Figure 5:
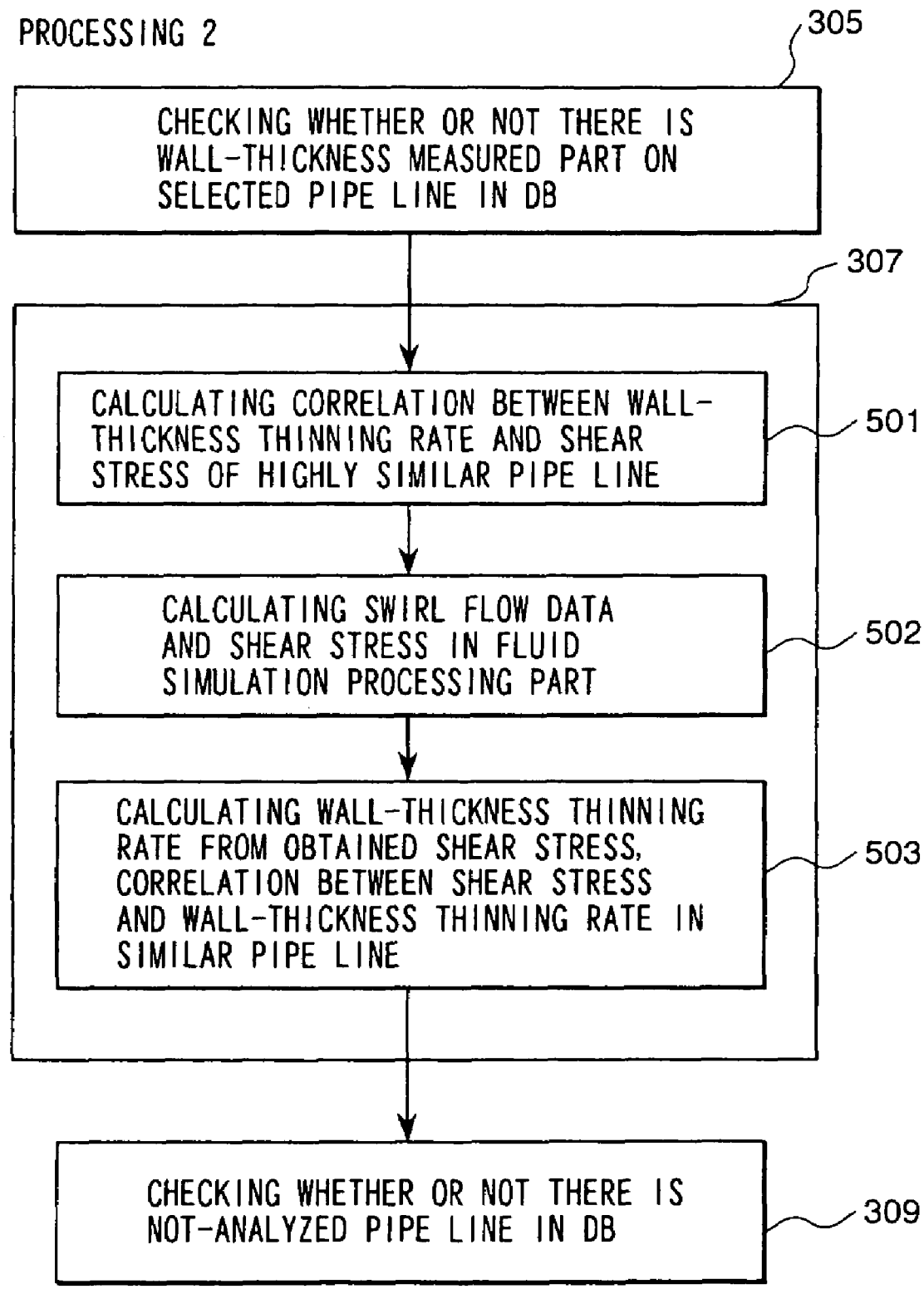
FIG. 5 is a flow diagram of Process 2.

The flow of Processing 2 will be described below, referring to FIG. 5.

A correlation between the wall-thickness thinning rate and the shear stress of a similar pipe line (Process 501). The correlation here means the wall-thickness thinning rate per unit force of the shear stress.

In the fluid simulation processing part, the swirl flow data of the pipe line is calculated and the shear stress is calculated (Process 502), and the wall-thickness thinning rate is calculated from the calculated shear stress and the correlation between the shear stress and the wall-thickness thinning rate in the similar pipe line (Process 503). These processes 502 and 503 are similar to that in the processes of Processing 1.

The estimated wall-thickness in the future is calculated by multiplying a period to the wall-thickness thinning rate.

Figure 6:
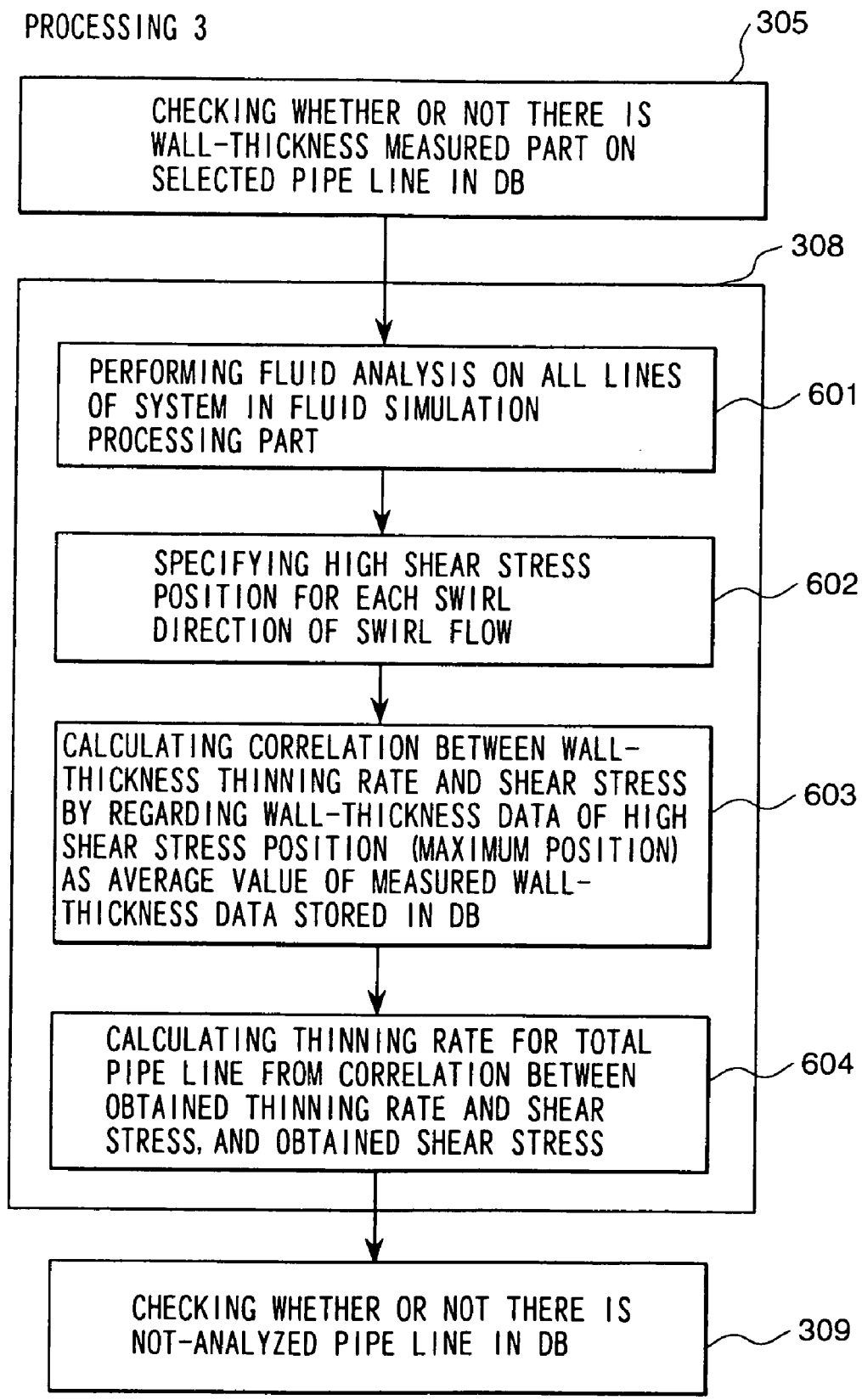
FIG. 6 is a flow diagram of Process 3.

The flow of Processing 3 will be described below, referring to FIG. 6.

By performing fluid analysis on all the lines of the system in the fluid simulation processing part (Process 601), the shear stress for each swirl direction of the swirl flow to specify a position where the value of the shear stress is high (Process 602).

It is assumed that the wall-thickness data at the high shear stress position (the highest shear stress position) is the average value of the measured wall-thickness data stored in the DB. Under the premise, the correlation between the wall-thickness thinning rate and the shear stress is calculated.

A wall-thickness thinning rate of each piping part in the pipe line is calculated from the calculated correlation between the wall-thickness thinning rate and the shear stress and the shear stress. The estimated wall-thickness in the future is calculated using the wall-thickness thinning rate.

The replacing work plan planning processing 116 will be described below. Before described the replacing work plan planning processing 116, a method of planning a piping modification work plan for a process plant will be described in detail, taking a nuclear plan as an example. Nuclear plant modification work is safely performed usually by closing a valve of a modification work zone to isolate from the other zones (system isolation). During the modification work period, operation of the plant is usually stopped in order to secure the safety.

On the other hand, the piping replacement in the nuclear plant is performed in the procedure of "setting up of a "scaffold" necessary for the replacing job; "decontamination job" for reducing the radiation dose in the pipe; "cutting" of the pipe line to be worked; "disposition" for currying out the cut piping part; "installation" for attaching a new piping part; "welding" of the installed piping part; and finally "painting" for protecting the outside of the attached pipe from the environment. There are many jobs in each of the procedure processes.

Estimation of period and cost required for each job is necessary for making the schedule plan. The job period and the job cost are calculated based on man-hours required for the job (job man-hour). The job man-hours is expressed by a product of number of pipes (material amount) and working hours of workers (job cost).

That is, the job man-hours can be expressed by Equation 6.

Job man-hours=(material amount)×(job cost)  (Equation 6)

Further, the schedule of the jobs other than the installation and the welding may be reduced by commonly using the scaffold, and by eliminating work for preparing machines used for the jobs.

That is, in the jobs other than the installation and the welding, there are jobs of which the man-hours do not depend on the material amount. Therefore, the job man-hours can be expressed by Equation 7.

Job man-hours=((material amount)×(job cost))$_{scaffold\ set}$+((material amount)×(job cost))$_{decontamination}$+((material amount)×(job cost))$_{cutting}$+((material amount)×(job cost))$_{disposition}$+((material amount)×(job cost))$_{installation}$+((material amount)×(job cost))$_{welding}$+((material amount)×(job cost))$_{painting}$ (Equation 7)

Further, a cost of work can be calculated by taking the work period and the cost of employing workers during the work period based on the job man-hours.

The total piping work cost can be calculated from Equation 8.

Total piping work cost=work cost+electric power loss due to plant shutdown+piping material cost (Equation 8)

Since the electric power loss and the work cost can be reduced by performing replacement of plural pipes together at a time, the total maintenance cost during the plant servicing period can be optimized.

The system structure will be described below.

The DB 113 comprises the DB 1302 which stores the results of estimating the wall-thickness thinning of the piping parts performed by the pipe wall-thickness thinning prediction processing 115, and the estimated wall-thickness data to be output.

The estimated wall-thickness data is input to the replacing work plan planning processing 116 from the DB 1302.

The replacing work plan planning processing 116 is composed of a replacing timing combination generating part 1305, which makes a plurality of long-term plant maintenance plans by extracting and receiving accurate lifetimes and remaining lifetime periods of the plant components from the estimated wall-thickness data and by selecting plant components to be modified in taking the lifetimes of the plant components; a maintenance cost calculation part 1303, which calculates the costs required for the plant maintenance plans by calculating job man-hours from the plant maintenance plan data and the job procedure, the piping material amounts and the job cost data, and by calculating the work cost from the job man-hours and the loss associated with the shutdowns during the work periods, and by summing the costs together with the material costs; and an optimum work plan determining part 1304, which selects a maintenance plan optimizing the cost and the reliability during the plant servicing period in taking needs of the client into consideration from all the plant maintenance plans after calculating and recording all the maintenance costs for all the plans.

Figure 14:
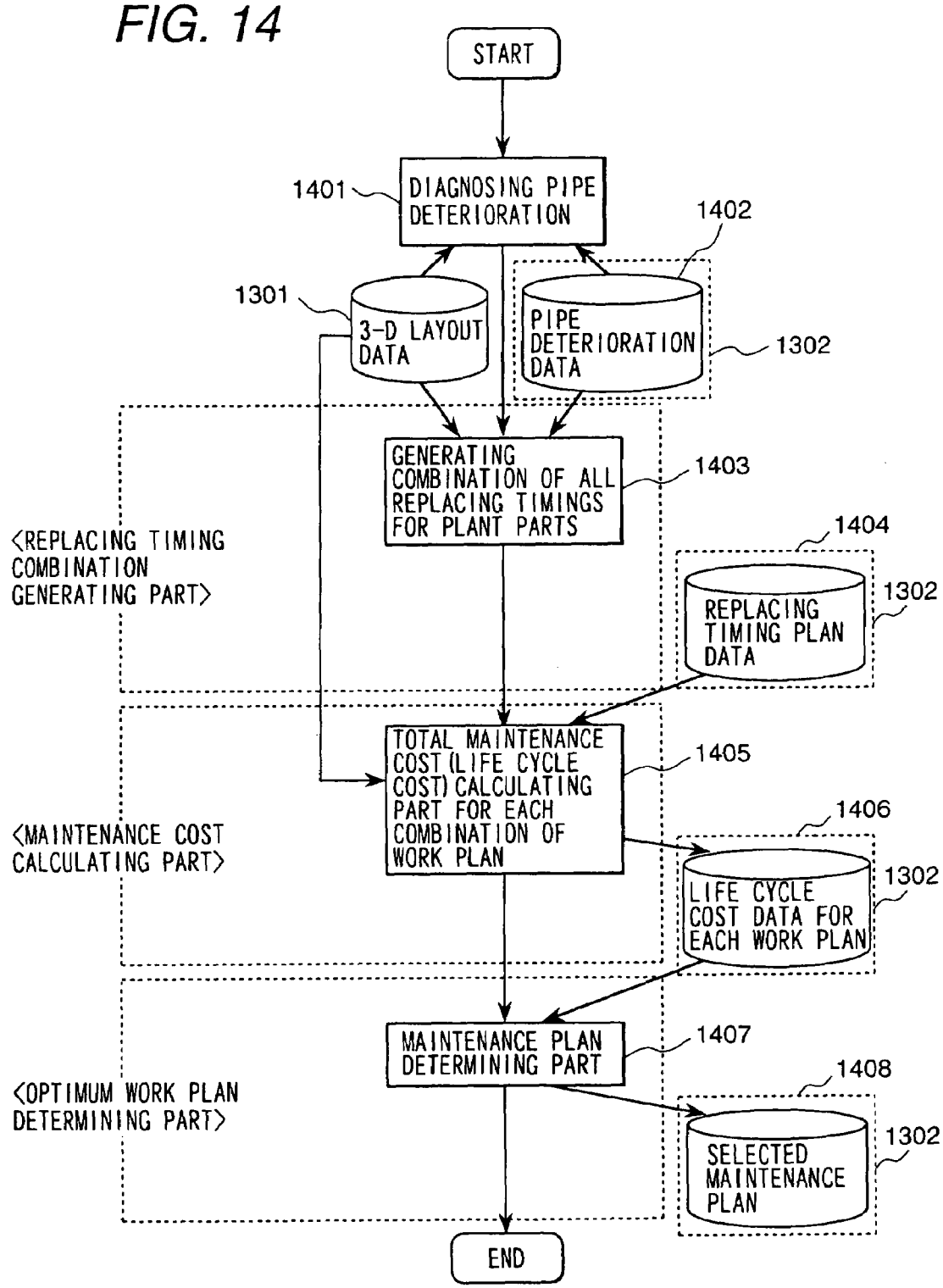
FIG. 14 is a diagram showing the processing flow of the replacing work plan planning processing.

The processing flow executed in the replacing work plan planning processing 116 will be described below, referring to FIG. 14.

Initially, estimation of wall-thickness thinning of the piping parts is executed in the pipe wall-thickness thinning prediction processing 115, and the estimated wall-thickness data is stored in an area 1402 in a pipe deterioration database 1302 as pipe deterioration data. The pipe deterioration data and the three-dimensional piping layout data are input to the <replacing timing combination generating part 1305>, and all combinations of individual plant part replacing timings are output (Process 1403) and then stored in a replacing timing plan database 1404 as work plan data.

The recorded work plan data is output to the <maintenance cost calculating part 1303>, and the maintenance costs for the individual work plans are output (Process 1405), and stored in a life-cycle cost database of each of the work plans. The maintenance costs for the individual work plans are input to the <optimum work plan determining part 1304>, and the most economical maintenance plan is determined among the individual work plans (Process 1407).

The construction of each of the processing parts in the replacing work plan planning processing and the processing flow will be described below in detail.

Figure 15:
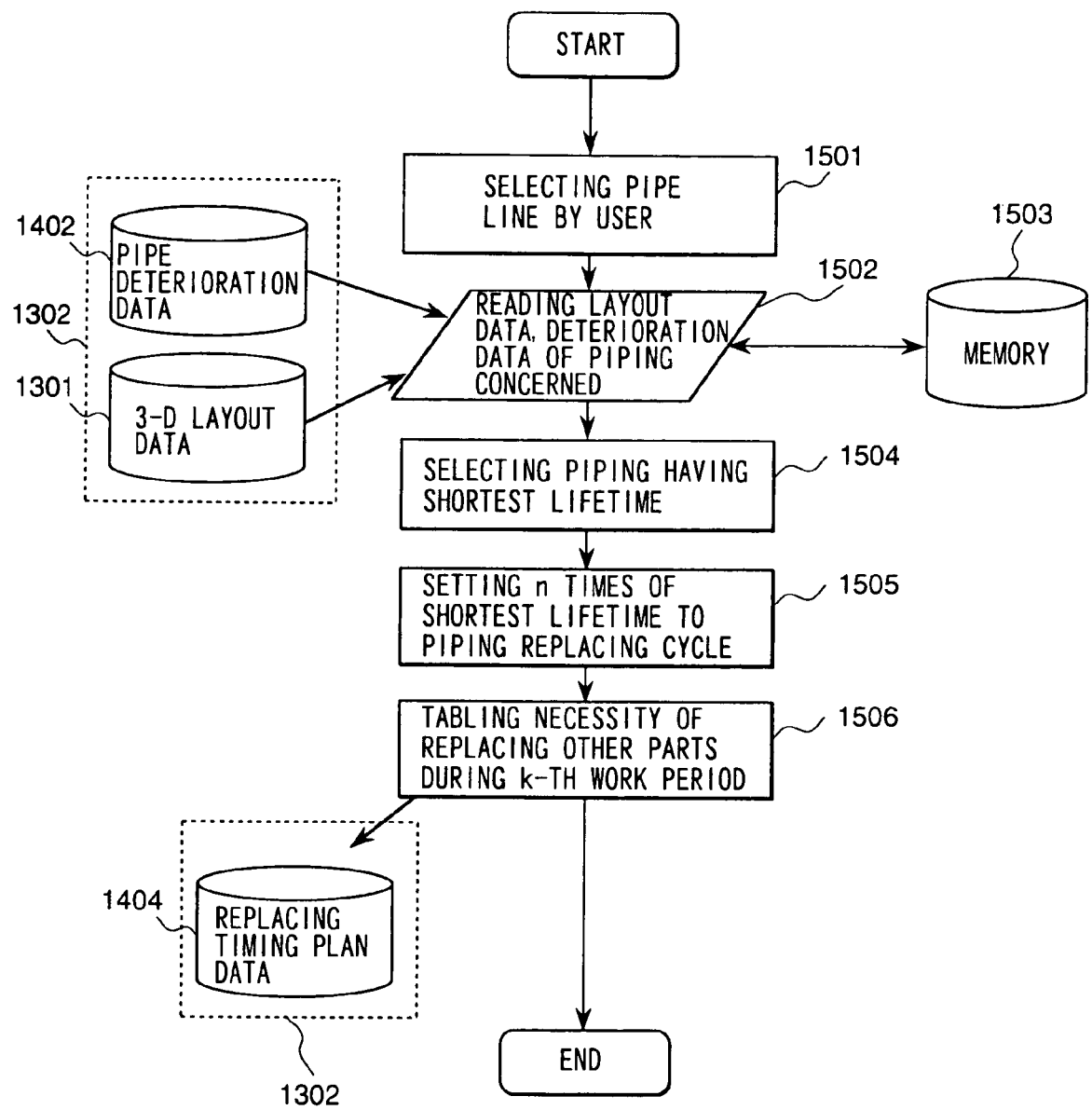
FIG. 15 is a diagram showing the processing flow of the replacing timing combination generating part.
Figure 16:
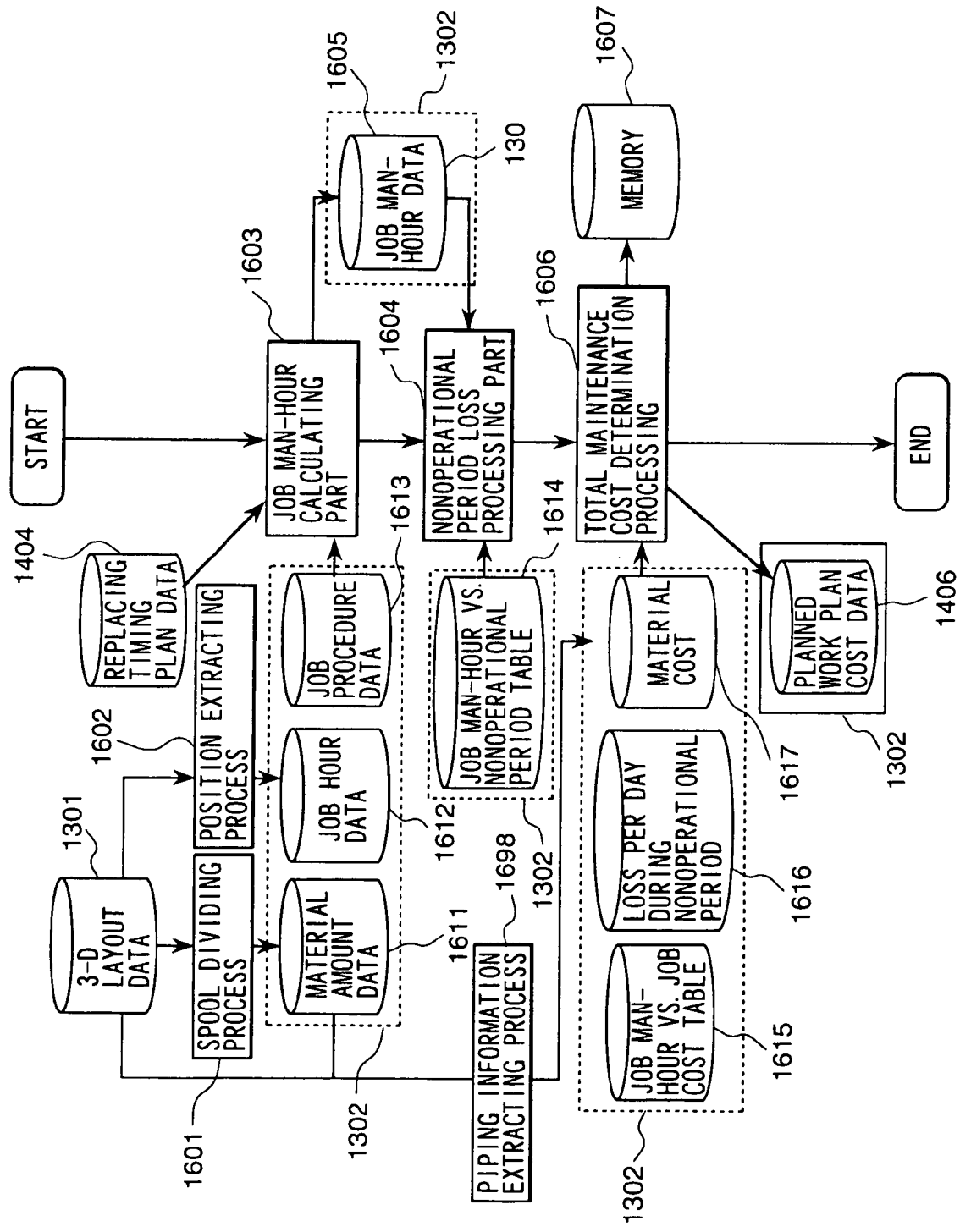
FIG. 16 is a diagram showing the processing flow of the maintenance cost calculation part.

Firstly, the <replacing timing combination generating part 1305> will be described, referring to the processing flow of FIG. 15.

A pipe line is selected by inputting a piping part ID directly from the key board or the mouse, or being sent through the communication units (Process 1501). A lifetime of the pipe part of the pipe line selected using the piping part ID as the key is extracted from the pipe deterioration database. The lifetime is input to the replacing timing combination generating part. Further, N-number of piping part IDs on the pipe line including the piping part are automatically searched from the pipe deterioration database, and the information on the piping parts are also input (Process 1502).

Next, a piping part having the shortest lifetime is searched from the N-number of piping parts having their lifetimes (Process 1504). Letting the lifetime of the piping part be a, years of m times of the lifetime a (m=0, 1, 2, 3 . . . ), that is, a×m year are set to a work period (Process 1505). Cases where the other parts cannot help being replaced during the m-th work period are classified (Process 1506), and the classified case combination is output as data shown in FIG. 20 and stored in the replacing timing plan database 1404.

The construction of the <maintenance cost calculating part 1303> will be described below.

Figures 19, 21:
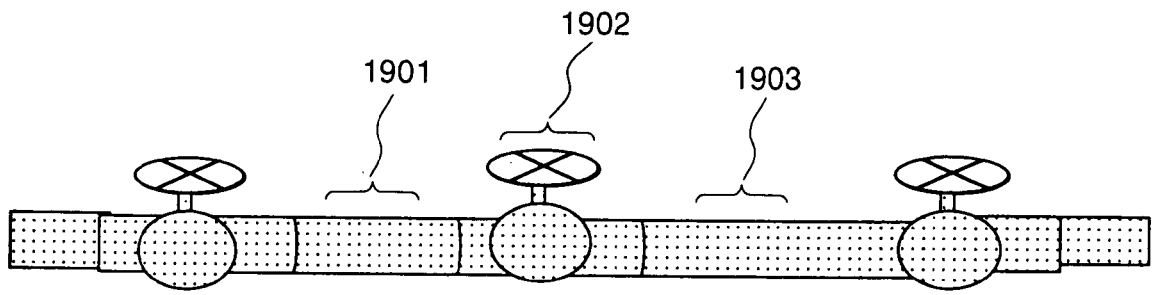
FIG. 19 is a view showing a pipe line.
FIG. 21 is a table showing material amount data.
Figure 26:
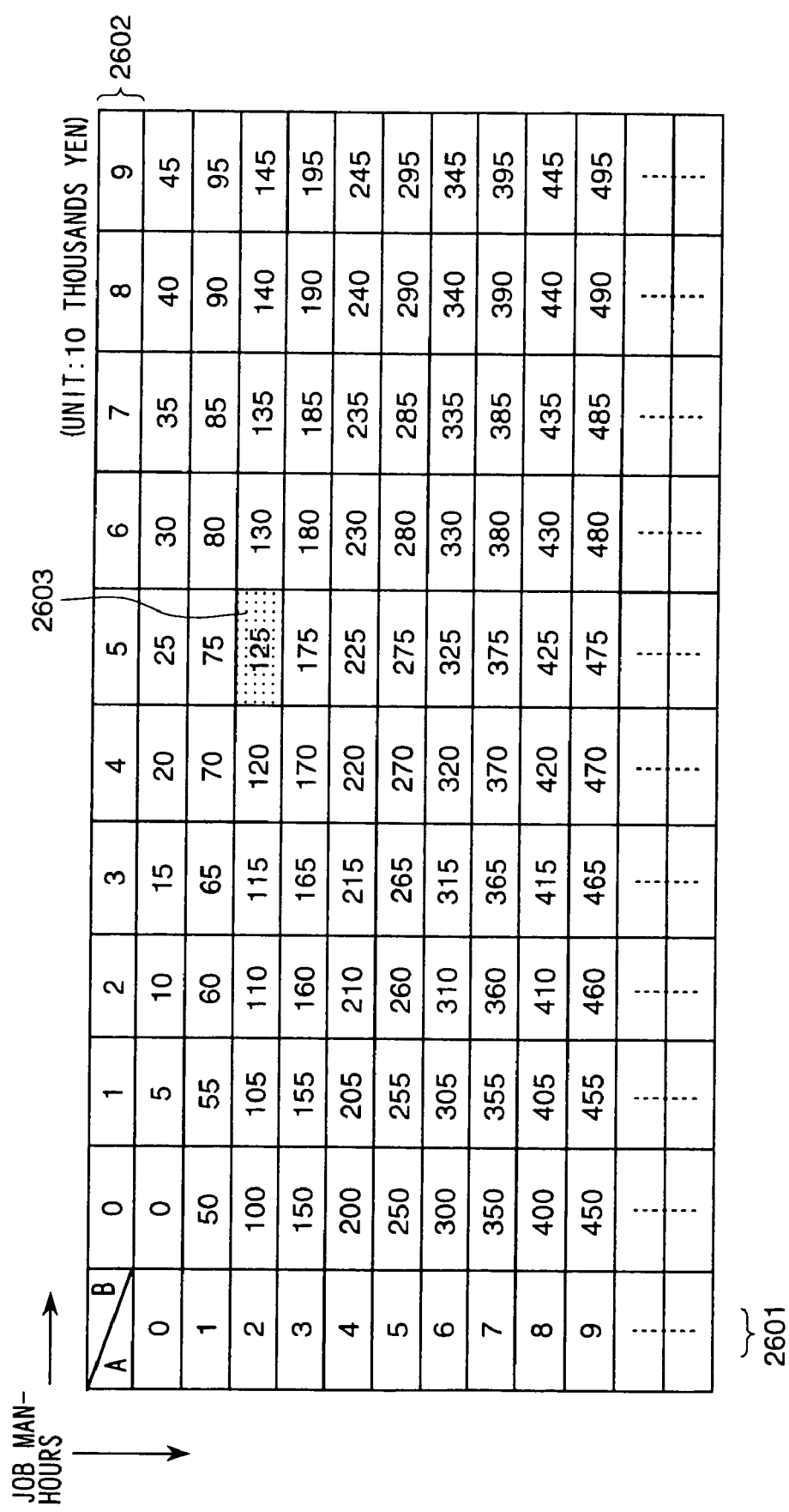
FIG. 26 is a job man-hour vs. job cost table.
Figure 27:
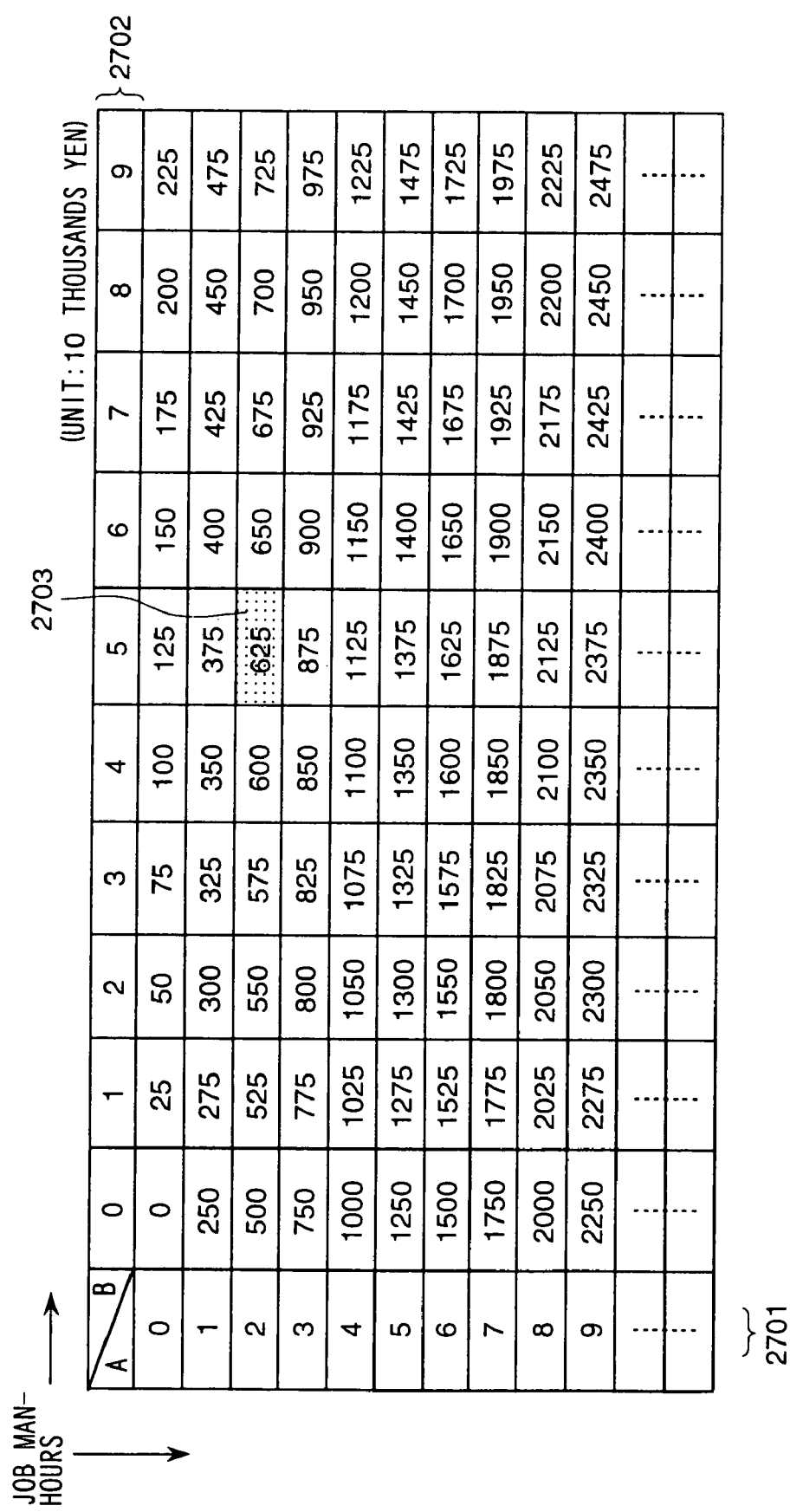
FIG. 27 is loss per day during non-operational period.

The <maintenance cost calculating part 1303> uses a material amount database 1611 as shown in FIG. 21 which is extracted from the three-dimensional information of piping; a job cost database 1612 which is formed the working hours of workers (job cost) in each job of the maintenance work in a data form as shown in FIG. 22; a job procedure database 1613 which is formed the job content for each work in a data form as shown in FIG. 23; a job man-hour vs. non-operational period table 1614 which is formed the job area and the plant non-operational period due to the work in a data form as shown in FIG. 25; a job man-hour vs. job cost table 1615 which is formed the job amount (job man-hour) and the job cost associated with the job man-hour in a data form as shown in FIG. 26; a loss par-one-day-shutdown database 1616 which is formed the loss per day associated with stopping the operation by closing the work area in a data form as shown in FIG. 27; and a material cost database 1617 in which costs per piping part are recorded as shown in FIG. 28.

The material amount database is formed by extracting data on lengths of pipes from the piping part three-dimensional layout database 1301 and being formed in a data form of the length for each pipe as shown in FIG. 21.

The job cost database records the summarized data in the data form of the job amounts for each job as shown in FIG. 22.

Figure 24:
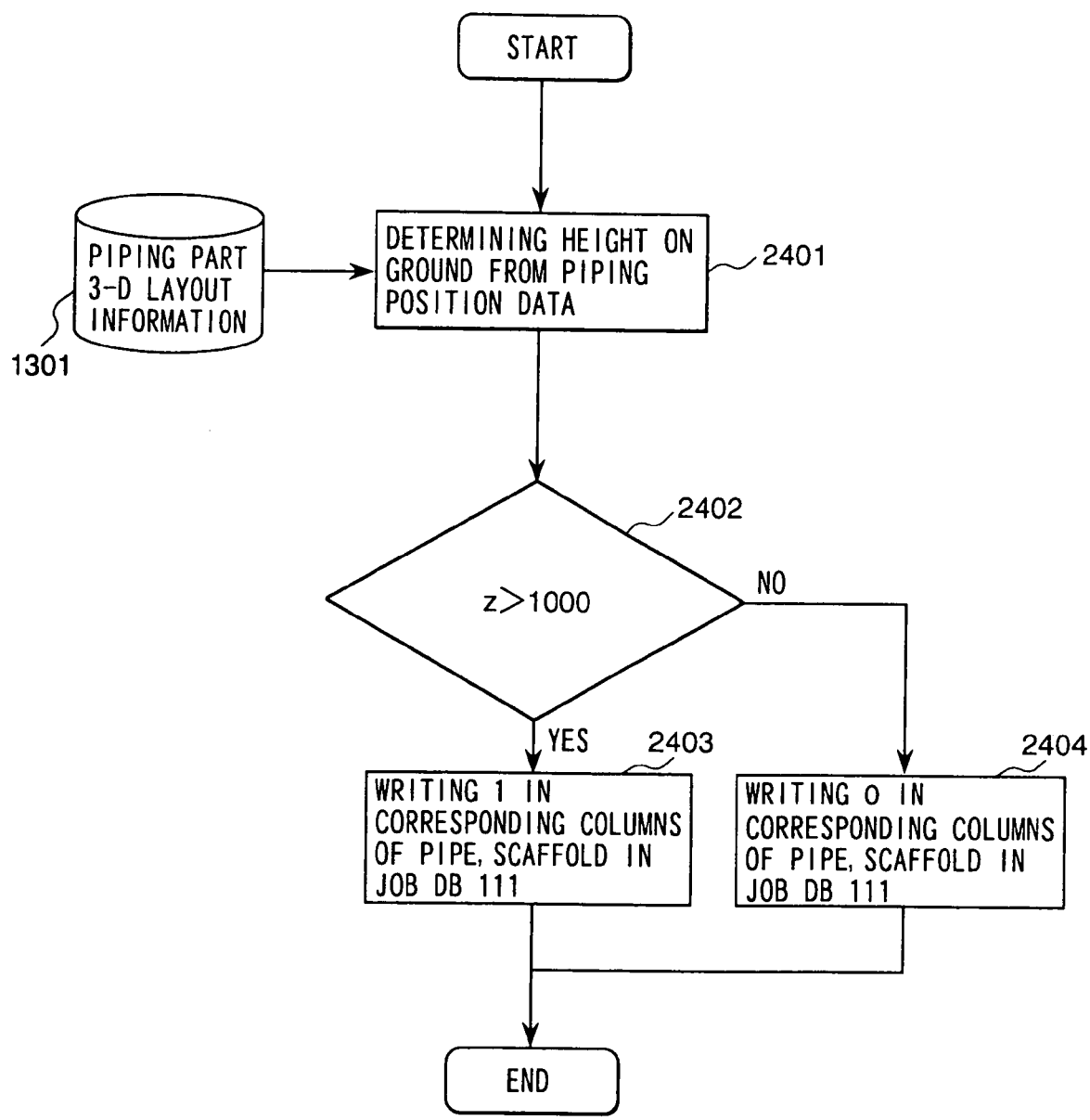
FIG. 24 is a flowchart showing generation of the job procedure data.

The job procedure data records the summarized data as shown in FIG. 23 on whether or not a job accompanied by each of the plant component should be performed. Therein, the numeral 1 in the table expresses that the job should be performed, and the numeral 0 expresses that the job should not be performed. This processing is executed according to the flow shown in FIG. 24. Further, a z-coordinate is determined from the pipe coordinate by linking the three-dimensional layout database 1301 and this database (Process 2401).

A height from the ground is determined and extracted, and it is judged whether or not the height is above 1 m (Process 2402). If above 1 m, the numeral 1 is recorded in the scaffold job column in the job procedure data (Process 2403). If below 1 m, the numeral 0 is recorded in the scaffold job column in the job procedure data (Process 2404).

The job man-hour vs. non-operational period table 1614 records the summarized data as shown in FIG. 25 by empirically determining work periods accompanied job man-hours from the job man-hours.

The job man-hour vs. job cost table 1615 records the summarized data as shown in FIG. 26 by calculating an empirical cost required for the job man-hours in the job procedure. Further, this data may be always updated in taking variations of prices and employment situation into consideration.

The loss par-one-day-shutdown database 1616 records the summarized data of an electric power loss per day due to stopping of the operation associated with the work as shown in FIG. 27.

The material cost database 1617 stores the summarized data of the pipe cost as shown in FIG. 28 by searching the material, the diameter and the length of the pipes from the three-dimensional database using the work objective pipe ID as the key recorded in the memory 1607 (piping information extracting processing).

Further, the material cost database 1617 can be connected to the vendor system through the communication unit, and accordingly can record the resent price and the delivery date of the piping parts using the information of the vendor. This system can make a work plan reflecting the material delivery data and the market.

Figure 33:
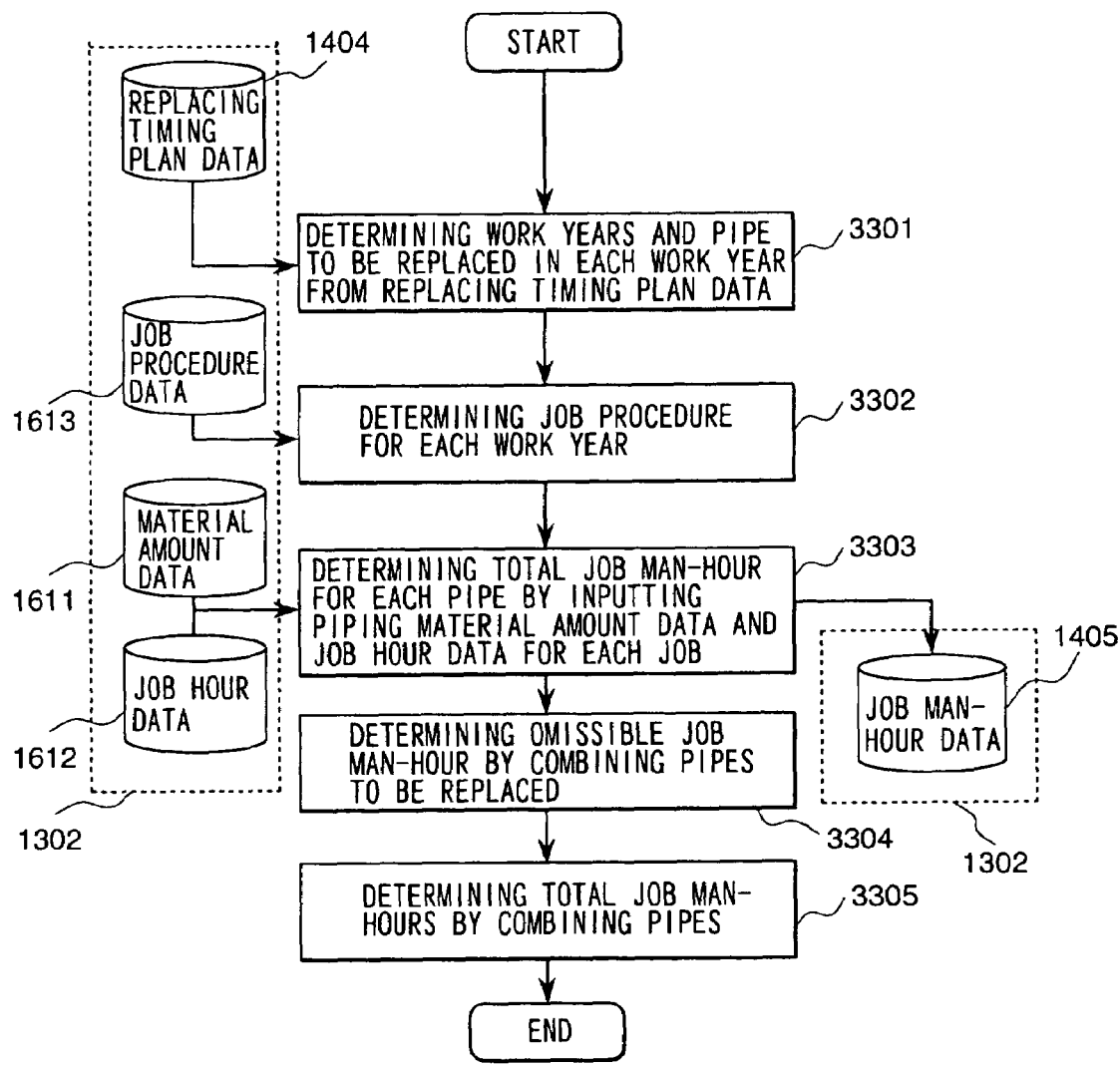
FIG. 33 is a flowchart showing the processing of the maintenance cost calculation part.
Figure 34:
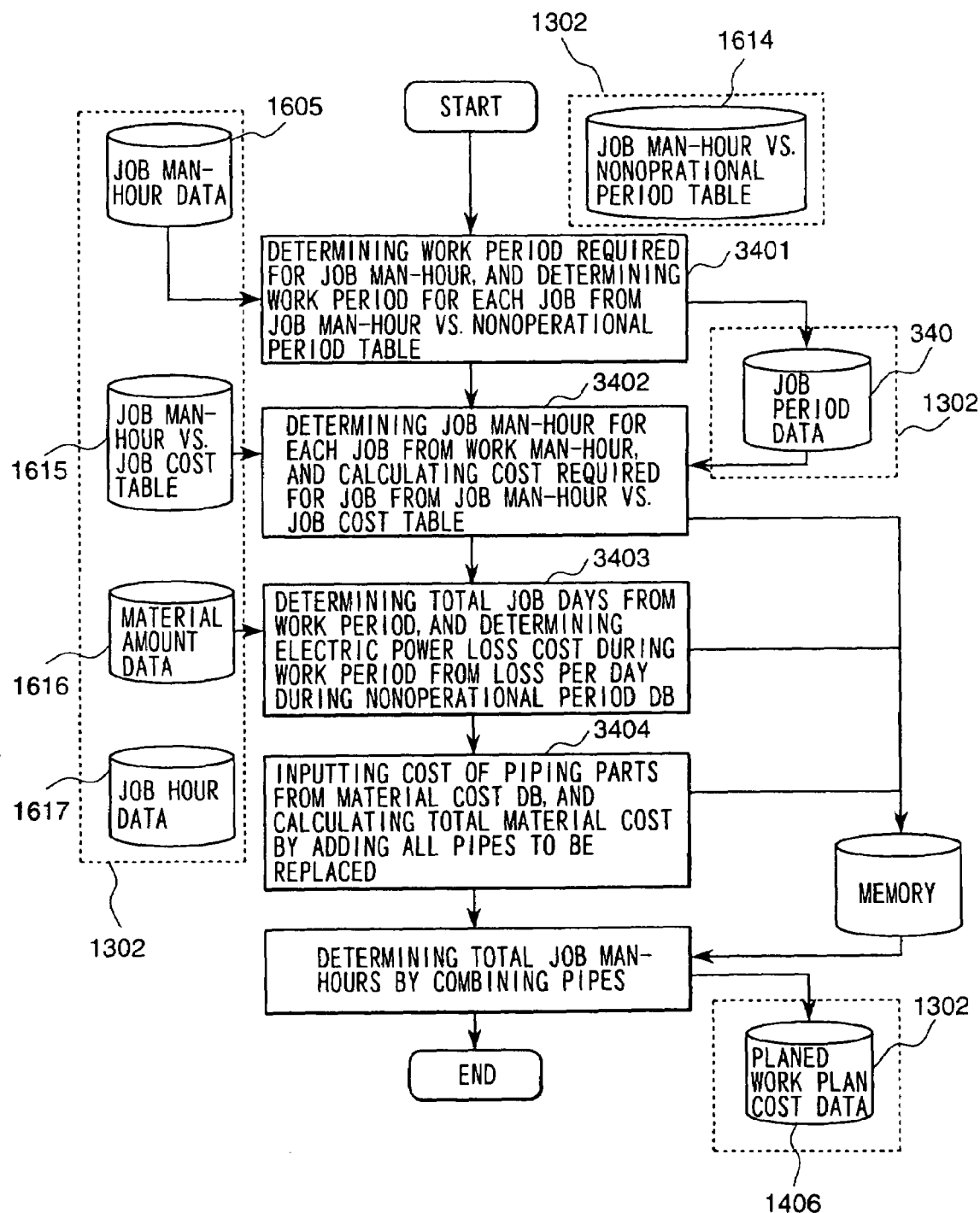
FIG. 34 is a flowchart showing the processing of the maintenance cost calculation part.

The processing flow of the <maintenance cost calculating part 1303> will be described below, referring to FIG. 33 and FIG. 34.

Firstly, the job plan data is input to the job man-hour calculating part from the replacing timing plan database. Pipes to be replaced in each work year are determined by obtaining information on the job man-hour part from the area 2002 and information on the replacing work timing from the area 2003 (replaced 1, not-replaced 0) (Process 3301).

It is determined from the job procedure data 1613 of the corresponding pipe using the work objective pipe ID as the key whether or not each of the process jobs is to be performed (job is required 1, job is not required 0). Then, each job man-hours is calculated using Equation 6 (Process 3302).

Therein, the material data 1611 is input as the material amount of each job for each pipe, and the job cost data 1012 is searched and input as the job cost for each job. As the result, each of the job man-hours and the total job man-hours are output and stored in the job man-hour database.

Figure 36:
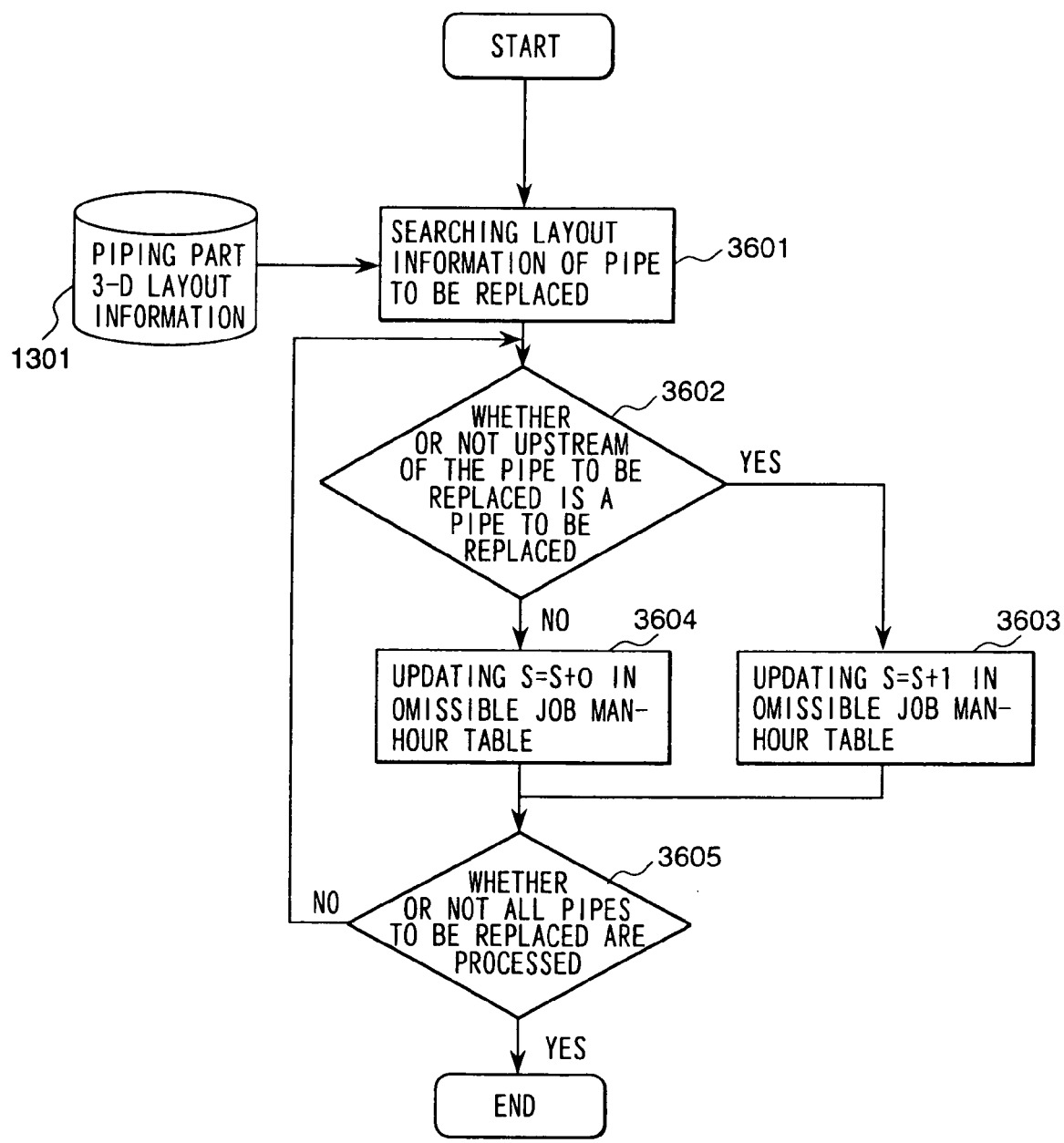
FIG. 36 is a block diagram showing the flow of generating omissible job man-hour data.

Further, the job man-hours required for the replacing jobs for all the selected pipes are individually summed for each of the jobs, and the result are additionally recorded in the area 2901 of FIG. 29 (Process 3303). Further, it is checked whether or not there are any omissible work objective pipe, and omissible job man-hours are determined. Whether or not each of the piping parts is omissible is determined according to the flow shown in FIG. 36 (Process 3304). The total job man-hours are determined by subtracting the omissible jobs man-hours from the individual job man-hours.

The non-operational period loss processing part determines the total of the each man-hours 2902 by receiving the job man-hour data of the area 2901 (Process 3401), and determines work periods for individual jobs from the job man-hour vs. non-operational period table 1614 (Process 3402), and outputs them as the job period data to be recorded as shown in FIG. 25.

This determining processing is performed as follows. Letting a job man-hour be 10×A+B (A, B: integers, B<10), the first column 2501 of FIG. 25 indicates A, and the first row 2502 indicates B. For example, a man-hour is 25, it is recognized that A=2, B=5 and the area 2503 in the figure is regarded as the required work period.

The total maintenance cost determining processing part determines the job man-hours for each job of the job man-hour database 1605, and calculates the cost required for the job from the job days vs. job cost table 1615 using the job man-hour as the key.

This determining processing is performed similarly to the processing performed by the job man-hour vs. non-operational period table. Letting a job man-hour be 10×A+B (A, B: integers, B<10), the first column 2601 of FIG. 26 indicates A, and the first row 2602 indicates B. For example, a man-hour is 25, it is recognized that A=2, B=5 and the area 2603 in the figure is regarded as the required work cost, and the cost for each job is recorded in the memory 1503 (1607).

Next, the total job days is determined, and the electric power loss cost during work period is determined from the loss per day during non-operational period database using the total job days as the key (Process 3403).

This determining processing is performed similarly to the processing performed by the job man-hour vs. non-operational period table. Letting a job man-hour be 10×A+B+(A, B: integers, B<10), the first column 2701 of FIG. 27 indicates A, and the first row 2702 indicates B. For example, a man-hour is 25, it is recognized that A=2, B=5 and the figure in the area 2703 is regarded as the electric power loss cost, and the cost is recorded in the memory 1503 (1607) in the form shown by FIG. 30.

Therein, the total cost of the piping parts is obtained by receiving cost 281 of the corresponding piping part from the material cost database 1617 using the pipe ID as the key, and by summing the costs for all the replaced pipes, and then recorded in the memory 1503 (1607) as the total material cost as shown by FIG. 31 (Process 3403).

The work cost, the loss cost and the material cost stored in the memory are processed as shown by Equation 8 to determine the total maintenance cost, and are recorded in the planned work plan cost database as shown by FIG. 32 by adding the individual cost 3202 to the work plan of FIG. 20 (Process 3405).

Figure 17:
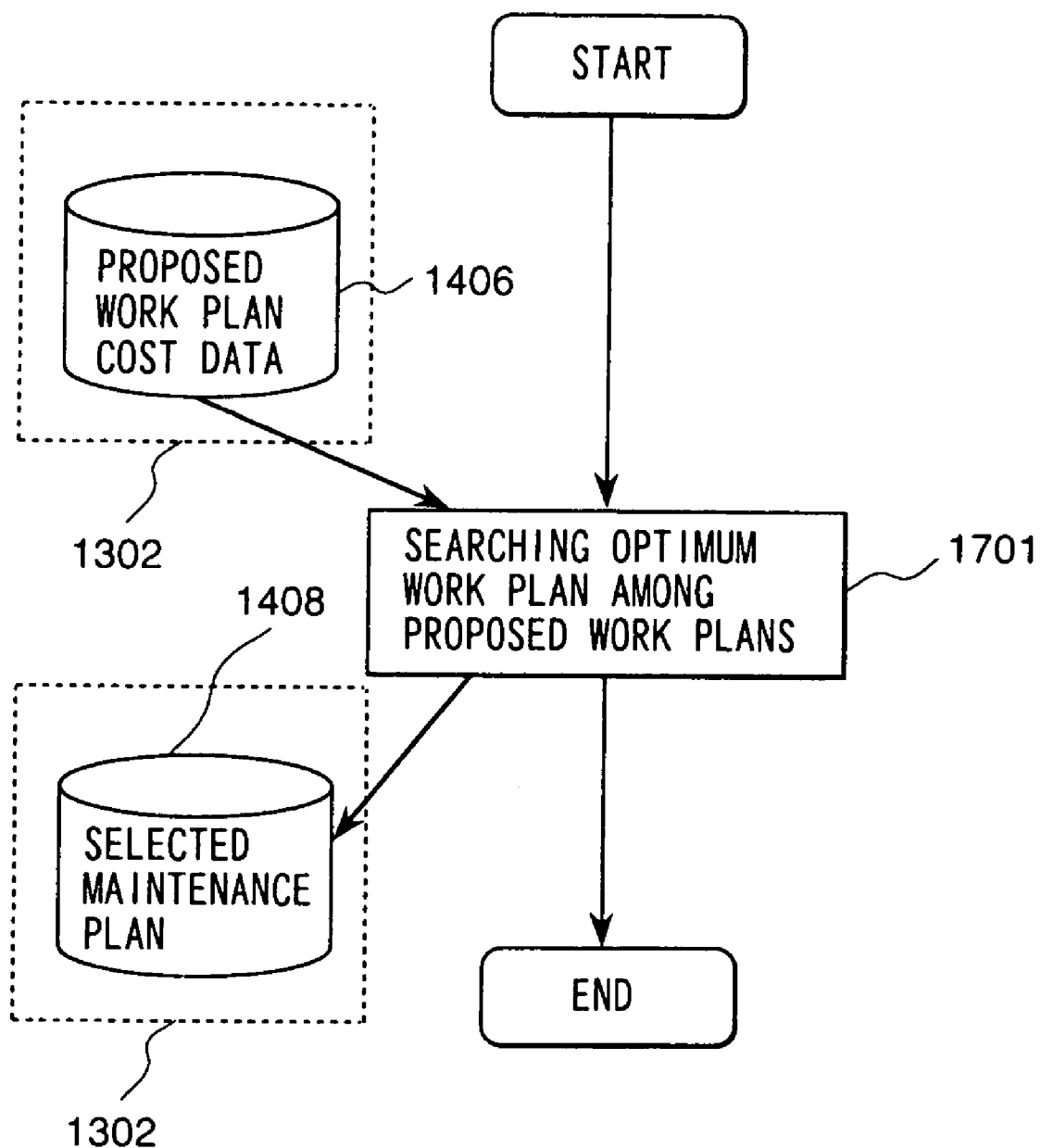
FIG. 17 is a diagram showing the processing flow of the optimum work plan determining part.

Finally, the processing flow of the <optimum work plan determining part> will be described, referring to FIG. 17.

The lowest cost is searched from the cost column of the work plan case classification table 3201 stored in the planed work plan cost database 1406 (Process 1701), and the plan is recorded in the optimum work plan database 1408.

The optimum work plan determining part can make a work plan which matches with an investment plan in maintenance by searching the maintenance cost for each work period from the maintenance plan stored in the planned work plan cost database.

Further, the optimum work plan determining part can make a work plan in which a used part or a part having a different lifetime for the replacing piping part.

A minimum cost pipe replacing work plane will be made below, taking an actual plant piping line as an example.

A pipe line composed of three piping parts 1901, 1902 and 1903 in a nuclear plant having a lifetime of 10 years is assumed, as shown by FIG. 19. Description will be made on a detailed processing flow of this pipe line in which the processing automatically makes a maintenance plan and minimizes the maintenance cost during the plant servicing period.

The piping parts have pipe IDs of PIPE-1(1901), VAL-1(1902) and PIPE-2(1903), respectively.

It is assumed that a piping part having a minimum lifetime and the lifetime is 3 years are determined by searching deterioration data in the pipe deterioration database 1402 using the pipe IDs as the key, and that the work period is three years (that is, the work is carried out in the first year, in the year 3 years after, in the year 6 years after, and in the year 9 years after). It is also assumed that the lifetimes of the piping parts are 3 years for PIPE-1(1901), 4 years for VAL-1(1902) and 9 years for PIPE-2(1903).

Cases whether or not VAL-1(1902) and/or PIPE-2(1903) are to be replaced is classified, and judgments whether or not there is necessity of replacement at n-th piping work period are stored in Table of FIG. 20.

This table classifies the cases that PIPE-1(1901) is to be replaced, and whether or not VAL-1(1902) and/or PIPE-2 (1903) are to be replaced. Replacing costs are calculated for each of the cases.

The first column of the table indicates combination number, the second column indicates the pipe IDs other than PIPE-1, and the third column and the columns after that indicate the work carrying-out years (the first row) and presence-and-absence of replacing work for piping parts other than PIPE-1(1901), and the numerals (1) and (0) indicate that the piping part is to be replaced and not replaced, respectively. In this example, number of the classified cases is 13, and the replacing plan becomes as shown by the table.

The pipe replacing plan No. 1 in the work plan case classification table is input to the plant maintenance cost calculation part, and the cost required for the pipe replacing plan No. 1 is calculated in the plant maintenance cost calculation part to record the work cost in the cost column of the work plan case classification table. The similar processing is performed on the pipe replacing plan No.=2, 3, . . . , 13, each of the costs is calculated and recorded.

Further, it is assumed that the work plan No.=1 of FIG. 20 is output from the replacing timing combination generating part. This work plan and the material amount data are input into the job man-hour calculating part, and the job cost is determined by each of the pipes and each of the kinds of work. The job man-hour can be calculated by the following (equation 9) from the (equation 7).

$$\text{Job man-hours} = ((\text{job cost}=18)_{scaffold\ set} \times (\text{material amount}=2)_{scaffold\ set}) + ((\text{job cost}=27)_{cutting} \times (\text{material amount}=1)_{cutting}) + ((\text{job cost}=24)_{decontamination} \times (\text{material amount}=8)_{decontamination}) + ((\text{job cost}=8)_{disposition} \times (\text{material amount}=3)_{disposition}) + ((\text{job cost}=25)_{installation} \times (\text{material amount}=3)_{installation}) + ((\text{job cost}=32)_{welding} \times (\text{material amount}=3)_{welding}) + ((\text{job cost}=6)_{painting} \times (\text{material amount}=3)_{painting})$$

(Equation 9)

Therefore, it is calculated that the first year work man-hours=300. In the case of this plan, since the similar work is to be performed 4 times during the plant lifetime, the total man-hour data becomes 300×4=1200.

The total man-hour data is input to the non-operational period loss processing part together with the job man-hour vs. non-operational period table. The non-operational period loss processing part searches the job man-hours=1200 cell among the job man-hour vs. non-operational period table, and outputs the corresponding job man-hours=2160 hours, that is, the job days=270 days, and calculates the work cost and the electric power cost accompanied by the work.

Therein, it is also possible to calculate the job period required for each procedure by using the job man-hours for each job procedure as the input data.

Since the work cost and the electric power cost are determined by the job man-hours and the job periods, the work cost and the electric power cost become 240 million yens and 96 million yens, respectively. On the other hand, it is assumed that the material costs are 1.00 million yens and 1.50 million yens for the pipes of PIPE-1, and -2, respectively, and 3.00 million yens for the valve of VAL-1, the total material cost becomes 22.00 million yens because of 4 times of replacement.

Thus, it can be obtained from (Equation 8) that

Work cost=2.200+240.00+96.00=358.00 (yens), and this result is stored in the cost column in the replacing timing plan database.

Finally, a plant maintenance work plan meeting with requirement of the client is searched from the work plan and the cost of the work plan case classification table in the optimum work plan determining part, and stored in the selected maintenance plan database. When the client requests a minimum cost work plan, the plans No. 8 and No. 12 are recorded in the selected maintenance plan database.

The series of the processing is performed on the 13 cases of the replacing plans output from the replacing timing combination generating part. The plant maintenance costs for all the cases are calculated.

The reason why the total maintenance cost differs depending on the cases will be explained, taking the maintenance plan No. 6 as an example.

In the maintenance plan No. 6, the pipes to be replaced are PIPE-1(1901), VAL-1(1902) and PIPE-2(1903) in the first year, and PIPE-1(1901), VAL-1(1902) and PIPE-2(1903) in the year after 3 years, and PIPE-1(1901) and PIPE-2(1903) in the year after 6 years, and PIPE-1(1901) and VAL-1(1902) in the year after 9 years. Number of pipes to be replaced in the years after 6 years and 9 years is smaller, and accordingly the material cost of the pipes and the job man-hour can be reduced.

Further, in the replacing work in the year after 9 years, the job man-hours can be reduced because of the continuous positional relationship of the replaced pipes. On the other hand, since the replaced pipes in the year after 6 years do not have the continuous positional relationship, the job man-hours can not be reduced so much.

As described above, the difference between the costs during the maintenance is caused by the differences in the material cost of the pipe and the job man-hours.

Description will be made below on comparison between a conventional maintenance work cost in which the plant parts are taken one by one and the maintenance work costs of the maintenance plans (No. 8 and No. 13) obtained from the present processing.

In the pipe line of FIG. 19, when the work plan is made through the conventional maintenance work cost in which the plant parts are taken one by one, the maintenance work must be performed 6 times, that is, in the years after 0, 3, 4, 6, 8, and 9 years.

On the other hand, in the work plan according to the present processing, the maintenance work is performed only 3 times, that is, in the years after 0, 3 and 6 years.

The electric power loss associated with stopping of plant operation can be reduced nearly one-half by the present processing.

Therein, the pipe work plan can be divided into a replacing preparation job from the scaffold setting to the piping part disposition; a main work from the installation to the welding; and the after settlement of the painting. The figure of the man-hours in the preparation work does not relate to the material amount. In other words, the man-hours when a plural number of piping part are replaced become nearly equal to those when a single piping part is replaced.

The reason is that when a plural number of piping part are replaced, number of cut position can be reduced and the scaffold can be commonly used. The decontamination job is not so much affected by the number of the piping parts. That is, the man-hours of the preparation job is nearly constant in each work regardless of the material amount.

Further, the costs required for the painting and the after settlement are nearly constant in each work. The work costs depending on the material amount are only the man-hours of the installation job and the welding job.

The material cost is 14.50 million yens in the maintenance plan No. 8, but 13.50 million yens in the conventional maintenance work.

From the above, the equation calculating the total maintenance cost can be also expressed as (Equation 10).

Total maintenance cost=(preparation job cost+after settlement job cost+loss cost due to stopping plant operation)×(number of work times)+(installation and welding job costs performed in each year)+(total material cost) (Equation 10)

When numerical values for the conventional method and the present system are substituted into (Equation 10), respectively, the following result can be obtained.

Total maintenance cost of the conventional method= (22.20+3.60+24.00)×6+(34.20+11.40+11.40+ 11.40+11.40+22.80)+13.50=414.90 million yens Total maintenance cost of the present system method= (22.20+3.60+24.00)×4+(34.20+22.80+34.20+ 11.40)+14.50==316.30 million yens Thus, the present processing can make a work plan more economical than that of the conventional method by 98.60 million yens.

According to the present invention, the predicted wall-thickness of the whole pipe line can be accurately obtained.

Further, the wall-thickness of a piping part other than the piping part of which the wall-thickness is measured can be predicted.

Further, the wall-thickness of a pipe line not having the piping parts of which the wall-thickness is measured can be predicted.

Furthermore, by making replacing work plans using these predicted result, more economical work can be performed.

What is claimed is:

1. A method of offering wall-thickness thinning prediction information in which wall-thickness data of piping parts for specifying wall-thickness values of the piping parts which may or may not be received from a client, and simulated wall-thickness data of the piping parts obtained based on the received wall-thickness data, if existent, is offered to the client, the method comprising the steps of:

simulating behavior of fluid flowing inside a pipe line based on said received wall-thickness data, if existent, of said piping parts and three-dimensional layout data of said pipe line including said piping parts using a computer;

calculating simulated wall-thickness data of said piping parts composing said pipe line in accordance with a change of said simulated behavior of fluid; and when said wall-thickness data of said piping parts and three-dimensional layout data of said pipe line including said piping parts is non-existent, calculating a prediction of a wall-thickness of said piping parts in accordance with a simulated data of said piping parts; and sending a simulated thinned wall-thickness data to the client.

* * * * *